(12) United States Patent
Xiang et al.

(10) Patent No.: US 12,728,287 B2
(45) Date of Patent: Sep. 8, 2026

(54) DEVICE AND METHOD FOR PROTOACOUSTIC IMAGE- GUIDED PROTON THERAPY

(71) Applicants: The Regents of the University of California, Oakland, CA (US); The Board of Regents of the University of Oklahoma, Norman, OK (US)

(72) Inventors: Liangzhong Xiang, Oakland, CA (US); Yong Chen, Oklahoma City, OK (US)

(73) Assignees: The Regents of the University of California, Oakland, CA (US); The Board of Regents of the University of Oklahoma, Norman, OK (US)

( * ) Notice: Subject to any disclaimer, the term of this patent is extended or adjusted under 35 U.S.C. 154(b) by 22 days.

(21) Appl. No.: 18/575,470

(22) PCT Filed: Jun. 29, 2022

(86) PCT No.: PCT/US2022/035594
§ 371 (c)(1),
(2) Date: Dec. 29, 2023

(87) PCT Pub. No.: WO2023/278627
PCT Pub. Date: Jan. 5, 2023

(65) Prior Publication Data

US 2024/0325788 A1 Oct. 3, 2024

Related U.S. Application Data

(60) Provisional application No. 63/217,110, filed on Jun. 30, 2021.

(51) Int. Cl.
*A61N 5/10* (2006.01)

(52) U.S. Cl.
CPC .......... *A61N 5/1049* (2013.01); *A61N 5/103* (2013.01); *A61N 5/1064* (2013.01); (Continued)

(58) Field of Classification Search
None
See application file for complete search history.

(56) References Cited

U.S. PATENT DOCUMENTS

2015/0314138 A1* 11/2015 Maurer ................ A61B 8/4263 600/1
2017/0128749 A1* 5/2017 Moskvin .................. A61B 8/08
(Continued)

OTHER PUBLICATIONS

International Search Report and Written Opinion on PCT Application No. PCT/US2022/035594 dated Sep. 23, 2022.

*Primary Examiner* — Hoon K Song
(74) *Attorney, Agent, or Firm* — FOLEY & LARDNER LLP

(57) ABSTRACT

Proton beams can deliver a highly targeted radiation dose to a narrow volume defined by their Bragg peaks. However, Bragg peak range uncertainties persist during dose delivery. Fortunately, pulsed proton beams generate protoacoustic emissions proportional to absorbed proton energy, thereby encoding dosimetry information in a detectable acoustic wave. The present embodiments provide methods and apparatuses to derive and model protoacoustic imaging with an ultrasound transducer, and examine the frequency characteristics of protoacoustic emissions, which are crucial parameters in imaging resolution.

19 Claims, 12 Drawing Sheets

(52) U.S. Cl.
CPC .... *A61N 5/1071* (2013.01); *A61N 2005/1058* (2013.01); *A61N 2005/1087* (2013.01); *A61N 2005/1092* (2013.01)

(56) References Cited

U.S. PATENT DOCUMENTS

| | | | |
|---|---|---|---|
| 2017/0165504 | A1 | 6/2017 | Dollinger et al. |
| 2021/0093897 | A1 | 4/2021 | Zadicario et al. |
| 2021/0138257 | A1 | 5/2021 | Dolgoff |

* cited by examiner

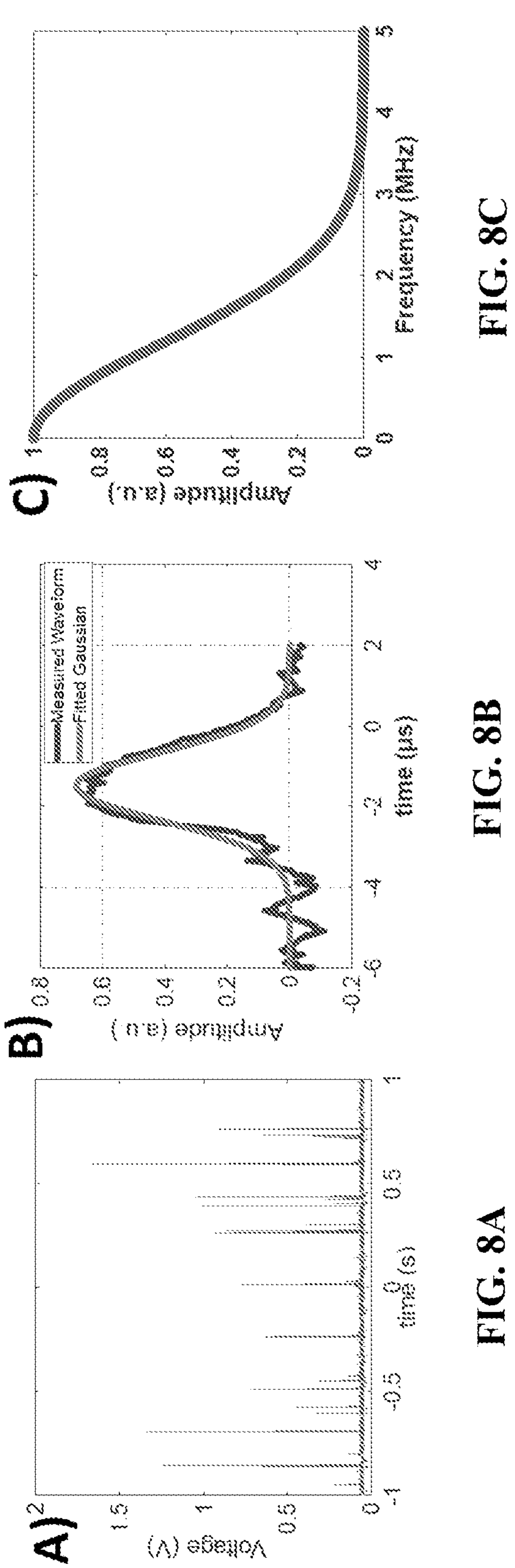
FIG. 8A
FIG. 8B
FIG. 8C
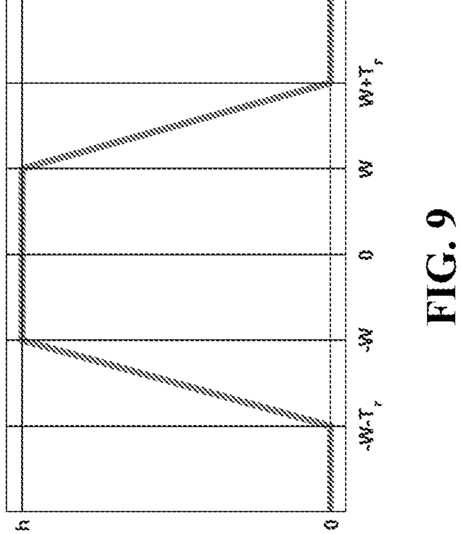
FIG. 9

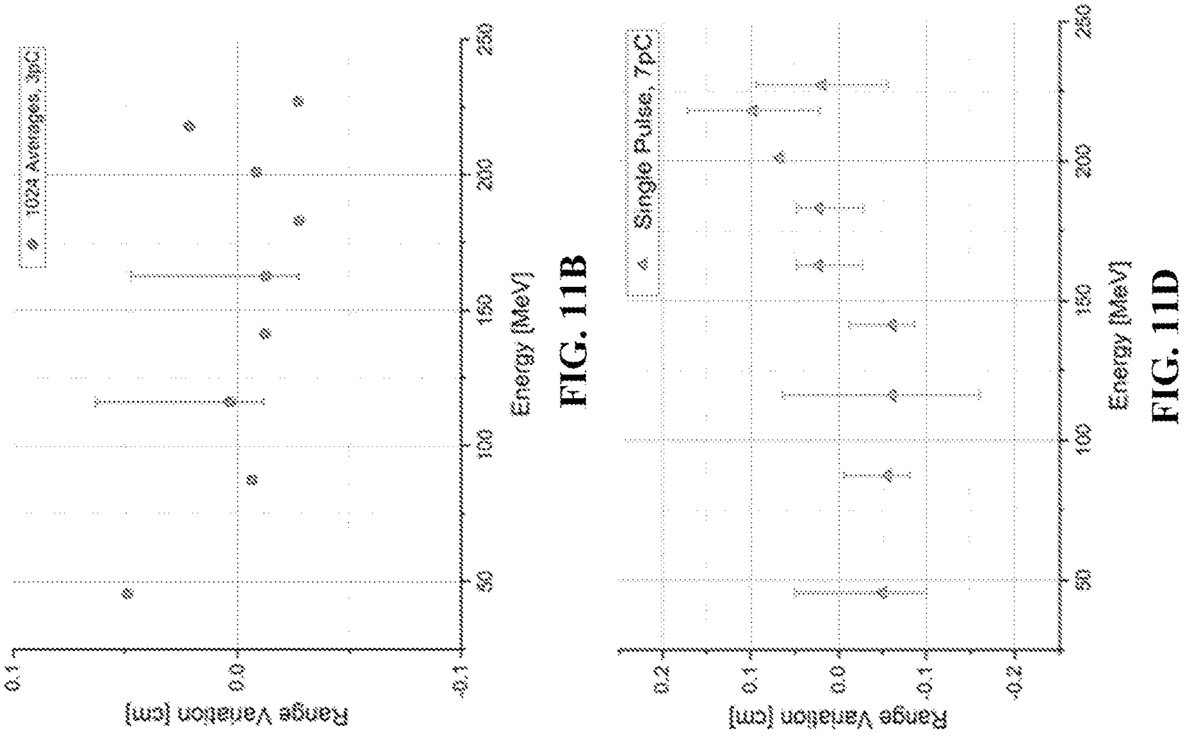
FIG. 11B
FIG. 11D
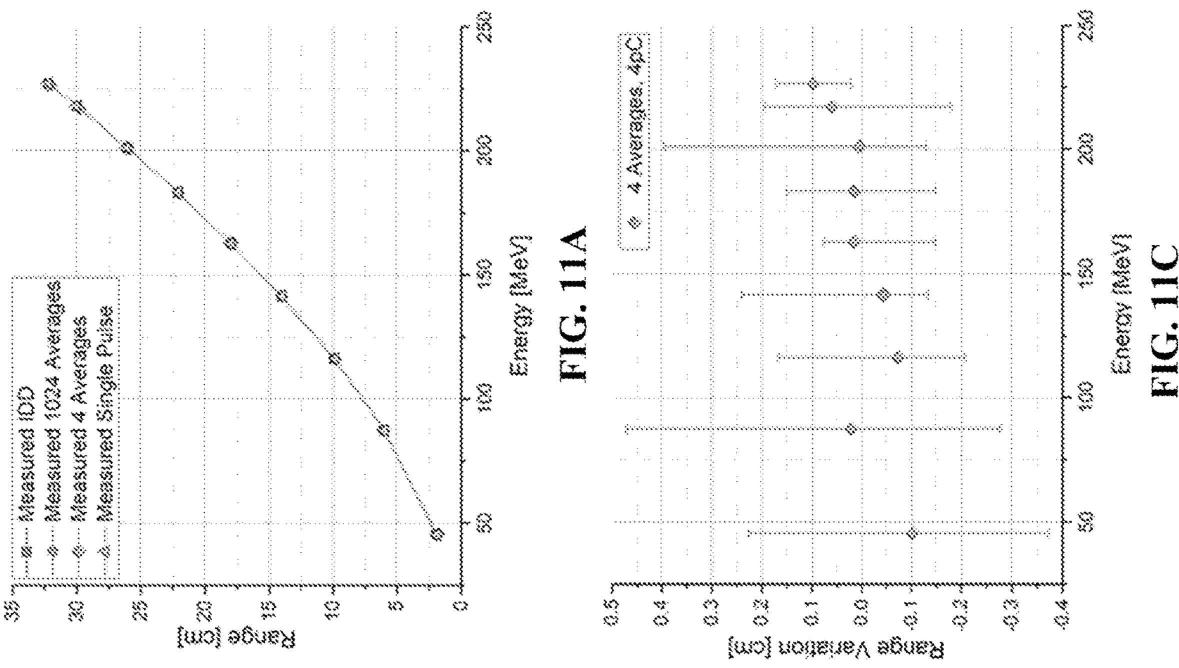
FIG. 11A
FIG. 11C

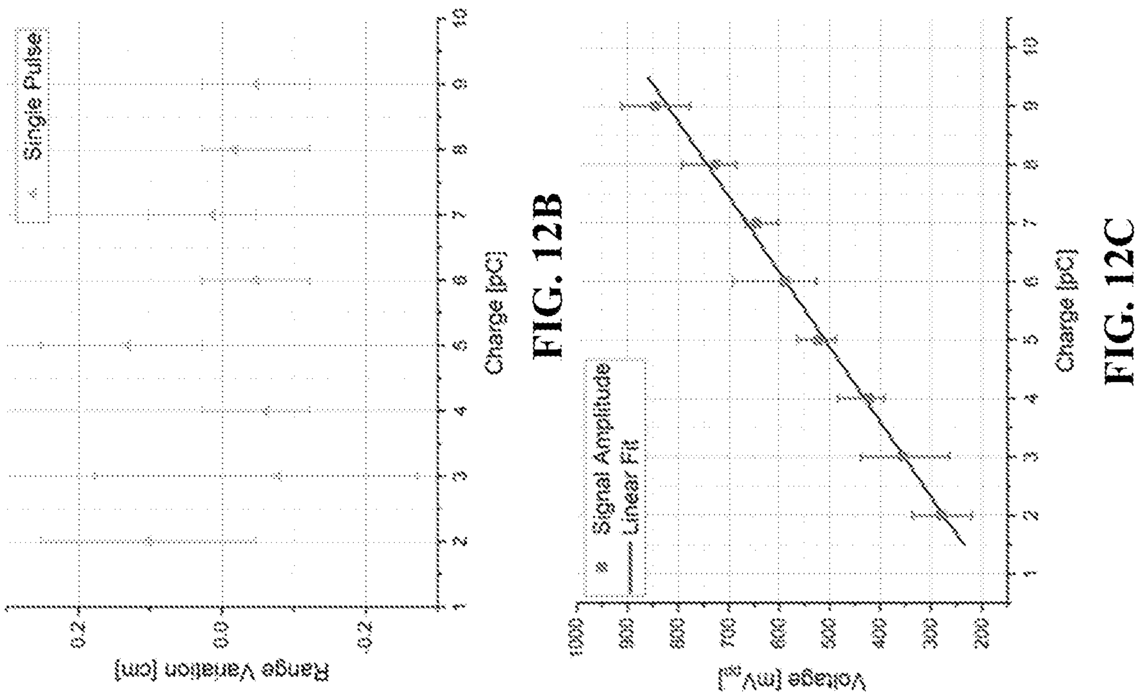
FIG. 12B
FIG. 12C
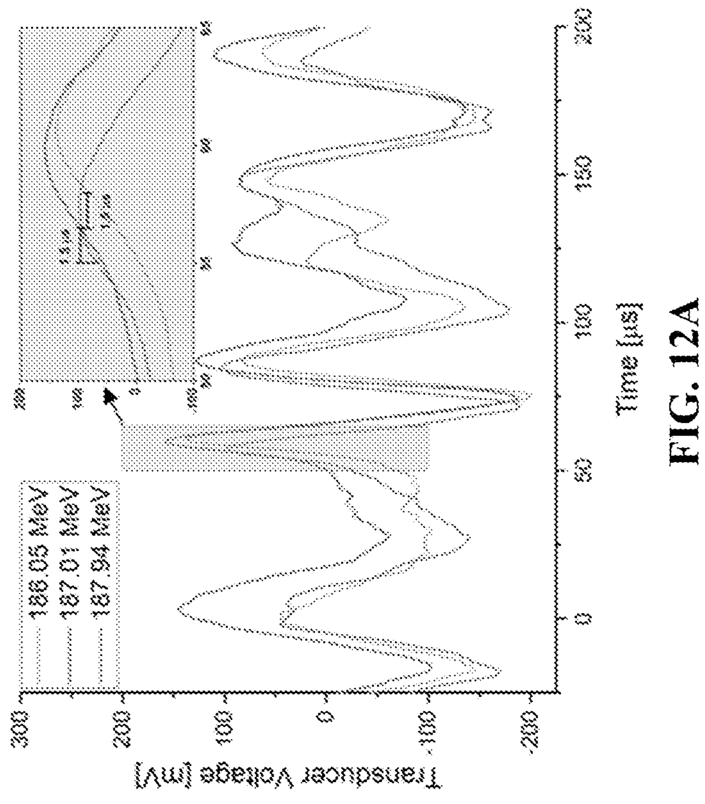
FIG. 12A

DEVICE AND METHOD FOR PROTOACOUSTIC IMAGE- GUIDED PROTON THERAPY

CROSS-REFERENCE TO RELATED APPLICATIONS

The present application is a National Stage Entry under 35 U.S.C. § 371 of International Application No. PCT/US2022/035594, filed Jun. 29, 2022, which is based on and claims priority to U.S. Provisional Patent Application No. 63/217,110 filed Jun. 30, 2021, the contents of which are incorporated herein by reference in their entirety.

TECHNICAL FIELD

The present embodiments relate generally to medical care and more particularly to methods and apparatuses for using protoacoustic imaging to assist proton therapy.

BACKGROUND

In radiation therapy, cancer tumors are targeted with ionizing radiation that induces cell death by damaging cancer cell's DNA. Radiation affects both malignant and healthy tissues, and treatment plans strive to deliver a lethal radiation dose to tumors while minimizing collateral damage to surrounding tissue. While conventional therapy employs X-ray photon radiation, the clinical use of proton radiotherapy is increasing because of its ability to localize dose just on the tumor. Compared to photons, which display an exponential decrease in deposition with penetration depth and induce radiation damage to normal organs, protons deposit a large fraction of their energy in the last few mm of their path due to the sharp distal falloff (see De Ruysscher D, Mark Lodge M, Jones B, et al. Charged particles in radiotherapy: A 5-year update of a systematic review. Radiotherapy and Oncology. 2012; 103(1):5-7. doi:10.1016/j.radonc.2012.01.003). The localized energy deposition position is called the Bragg peak. Because of the Bragg peak, tissue before and after the tumor receive a lower relative dose compared to conventional photon treatment. Therefore, the main advantage of proton radiotherapy for treatment of cancer is the Bragg peak. Unlike photons and electrons-based radiation therapy, the sharp dose falloff of the Bragg peak increases our ability to conform the treatment dose to the tumor and spare the surrounding healthy tissues. However, there are uncertainties that preclude the ability to precisely locate the proton beam Bragg peak within the patient in vivo, which often results in a deliberate over- and undershoot of the beam into healthy tissues located in front of and beyond the tumor (see Hickling S, Lei H, Hobson M, Léger P, Wang X, El Naqa I. Experimental evaluation of x-ray acoustic computed tomography for radiotherapy dosimetry applications. Med Phys. 2017; 44(2):608-617. doi:10.1002/mp.12039). This substantial increase to the margins undermines the benefits of the proton's unique steep dose gradient, reducing the clinical potential of proton radiotherapy.

To fully exploit the advantages of the proton therapy, there is a need to reduce proton beam range uncertainties especially at the distal edge where a sharp dose gradient exists. PET imaging and prompt gamma techniques have been proposed and tested as range verification techniques, but their lack of accuracy, complexity, and high cost which new technique is needed (Hickling S, Lei H, Hobson M, Léger P, Wang X, El Naqa I. Experimental evaluation of x-ray acoustic computed tomography for radiotherapy dosimetry applications. Med Phys. 2017; 44(2):608-617. doi:10.1002/mp.12039).

It is against this technological backdrop that the present Applicant sought to find a technological solution to these and other problems rooted in this technology.

SUMMARY

The present embodiments relate generally to methods and apparatuses that provide protoacoustic imaging to guide proton therapy. Embodiments include a protoacoustic method that can affordably verify the proton range and quantify the radiation dose in vivo. This approach can change how proton therapy is monitored and delivered and can reduce damage to healthy tissues. Embodiments further include a protoacoustic imaging prototype to localize the Bragg peak and measure the radiation dose in vivo with clinical proton therapy machine. These and other embodiments include tracking algorithms to verify the proton beam range, with sub-millimeter accuracy, through time-of-flight (TOF) and time-reversal acoustic measurements. These and other algorithms significantly reduce the error associated with variations in the speed of sound through heterogeneous tissues. Additional embodiments include hardware for protoacoustic signal acquisition and data processing. These and other embodiments use image reconstruction algorithms for protoacoustic image reconstruction. The system can be vendor-independent and can be translated for clinical use in patient monitoring. Relationships can be defined between the magnitude of acoustic signal production and the method for delivering the proton dose. The successful development of protoacoustic range-verification can provide a simple and inexpensive method for real-time, in vivo patient monitoring during proton irradiation with greater confidence in the proton range and consequently allowing smaller margins, increased sparing of healthy tissue, and improved patient outcomes.

BRIEF DESCRIPTION OF THE DRAWINGS

These and other aspects and features of the present embodiments will become apparent to those ordinarily skilled in the art upon review of the following description of specific embodiments in conjunction with the accompanying figures, wherein:

FIGS. 8A to 8C are diagrams illustrating aspects of pulse shape according to embodiments.

FIG. 9 illustrates an example Trapezoidal Pulse waveform according to embodiments.

FIGS. 11A to 11D are example graphs illustrating additional aspects of embodiments.

FIGS. 12A to 12C are example graphs illustrating additional aspects of embodiments.

DETAILED DESCRIPTION

Figures 1A, 1B, 1C:
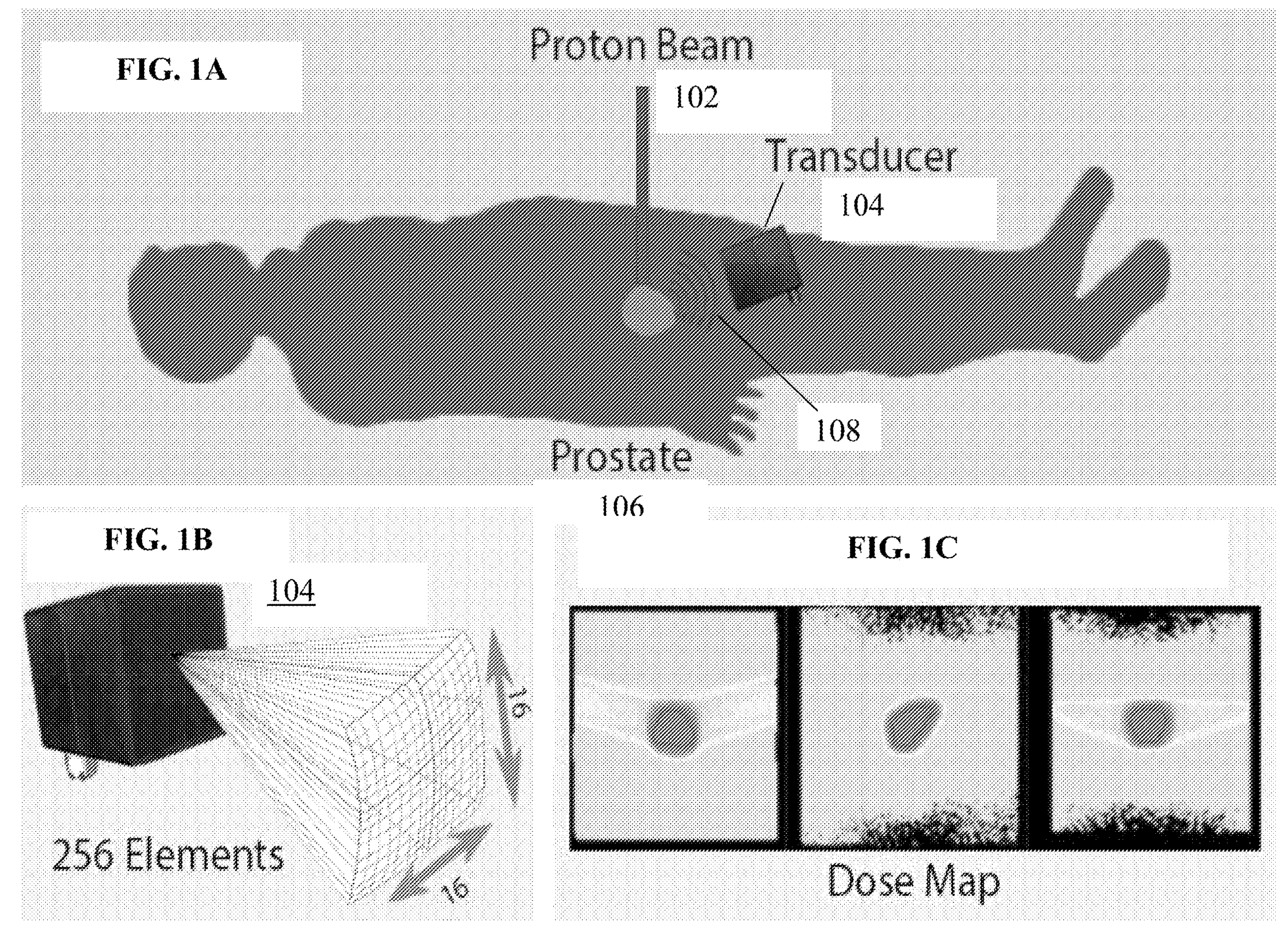
FIGS. 1A to 1C illustrate aspects of an example system according to embodiments.

The present embodiments will now be described in detail with reference to the drawings, which are provided as illustrative examples of the embodiments so as to enable those skilled in the art to practice the embodiments and alternatives apparent to those skilled in the art. Notably, the figures and examples below are not meant to limit the scope of the present embodiments to a single embodiment, but other embodiments are possible by way of interchange of some or all of the described or illustrated elements. Moreover, where certain elements of the present embodiments can be partially or fully implemented using known components, only those portions of such known components that are necessary for an understanding of the present embodiments will be described, and detailed descriptions of other portions of such known components will be omitted so as not to obscure the present embodiments. Embodiments described as being implemented in software should not be limited thereto, but can include embodiments implemented in hardware, or combinations of software and hardware, and vice-versa, as will be apparent to those skilled in the art, unless otherwise specified herein. In the present specification, an embodiment showing a singular component should not be considered limiting; rather, the present disclosure is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present embodiments encompass present and future known equivalents to the known components referred to herein by way of illustration.

INTRODUCTION

Among other things, the present embodiments can increase the precision of radiation delivery during proton radiotherapy by localizing the Bragg peak in real time. The protoacoustic image can provide the dosimetric information of the proton dose deposition in local tissue. The protoacoustic imaging can provide additional information and it is highly valuable during proton therapy since it can greatly improve the accuracy in tumor targeting and largely mitigate the undesirable collateral damage to surrounding normal tissues, thereby leading to a better patient outcome. An ultrasound device will provide 3D imaging capability for protoacoustic imaging.

As set forth above, the present Applicant recognizes that proton radiotherapy is of increasing importance and prominence in radiation oncology. This is because proton beams are capable of delivering a targeted dose in a narrow radiation volume defined by the Bragg peak of the proton beam. This narrow delivery of the dose allows for maximum dose delivery to the tumor region while minimizing dose delivery in surrounding healthy tissues. In contrast to x-ray based radiation therapy, the dose delivered to tissue from a proton beam is not highest near the surface, but instead inside the tissue at an adjustable, particle energy dependent depth.

The phenomenon of the Bragg peak has been widely exploited in multiple variations and applications of proton beams for radiation dosimetry, and has seen applications and potential in the treatment of brain cancers, prostate cancers, eye cancers, vascular diseases, skin cancers, and more.

Despite its promise, there remain some significant obstacles towards accurate proton radiation therapy, such as the inability to accurately localize the proton Bragg peak in 3D and/or in real-time. In current proton therapy clinical procedure, Bragg peak localization is calculated using a scouting CT, and then attempting to position the patient in a similar position to that in the simulations. However, the steep dose gradient of the proton Bragg peak is not always used to its full extent in practice. This is because there is substantial uncertainty about the proton beam range, which carries the risk of severely overdosing healthy tissues or under-dosing the target. The range uncertainty of proton beams has several sources, such as the non-uniqueness and inaccuracy of CT Hounsfield units to proton stopping power, CT imaging artefacts, and changes in the patient during treatment caused by mis-positioning, breathing, etc. Therefore, it remains an important clinical objective to achieve accurate proton range verification, ideally done through imaging and cross-correlation with known treatment plans.

Fortunately, the present Applicant recognizes that pulsed proton beams generate detectable acoustic emissions of proportional amplitude to the deposited dose. This 'protoacoustic' phenomenon presents a unique opportunity for range verification as well as dose imaging, as the Bragg peak itself is a high dose area and therefore a strong protoacoustic emitter. Therefore, with the simple addition of an ultrasound transducer with appropriate frequency bandwidth, real-time proton dosimetry is possible in vivo. Such a set-up is illustrated in FIGS. 1A to 1C. First, an incident pulsed proton beam 102 hits the prostate region 106, thus inducing a protoacoustic emission. This protoacosutic emission can be detected by an acoustic transducer. As shown in FIG. 1B, the transducer can be implemented using an ulstrasound transducer array (for example, a 16×16 element square array with element dimensions 1.2695 mm×1.2695 mm×2.5 mm) placed close enough to the acoustic source. So long as the array can capture the acoustic signal with acceptable signal-to-noise ratio, the transducer can be used to reconstruct a 3D image of the relative dose deposition of the beam (as shown in FIG. 1C, which provides an example of a dose map that could be reconstructed with this method, wherein deposition dose is linearly proportional to the protoacoustic signal).

In the context of protoacoustic research, there have been several simulation studies in the field examining different set-ups and problems. Recently, van Dongen et al (See van Dongen K W A, de Blécourt A J, Lens E, Schaart D R, Vos F M, "Reconstructing 3D proton dose distribution using ionoacoustics," Phys Med Biol. 2019; 64(22):225005. doi: 10.1088/1361-6560/ab4cd5) constructed a 3D simulation in which model-based inversion was deployed to reconstruct 3D dose distributions from simulated noisy pressure fields, taking tissue heterogeneities into account. However, delivery uncertainties (spot MU, spot position and AA positions) were not considered as the initial dose used was not calculated directly from the logfile of a clinical machine.

Assman et al (See Assmann W, Kellnberger S, Reinhardt S, et al., "Ionoacoustic characterization of the proton Bragg peak with submillimeter accuracy," Medical Physics, 2015; 42(2):567-574. doi: 10.1118/1.4905047) were impressively able to detect signals in 3D using a circular detector array scanned laterally, however in this setup lateral scanning is necessary and single shot 3D dose mapping is not possible. Ahmad et al (See Ahmad M, Xiang L, Yousefi S, Xing L, "Theoretical detection threshold of the proton-acoustic range verification technique," Medical Physics, 2015; 42(10):5735-5744. doi:10.1118/1.4929939) used a simulated system to determine the detection threshold in protoacoustic simulations, but did not simulate imaging. Jones et al (See Jones K C, Witztum A, Sehgal C M, Avery S., "Proton beam characterization by proton-induced acoustic emission: simulation studies," Phys Med Biol., 2014; 59(21): 6549-6563. doi: 10.1088/0031-9155/59/21/6549) and Yu et al. (See Yu Y, Li Z, Zhang D, Xing L, Peng H., "Simulation studies of time reversal-based protoacoustic reconstruction for range and dose verification in proton therapy," Medical Physics, 2019; 46(8):3649-3662. doi: https://doi.org/10.1002/mp.13661) performed detailed 2D simulations, but did not model full 3D propagation in their simulation studies. Recently, protoacoustic signals have been experimentally detected by a single low frequency acoustic f detector. However, a point-detector cannot determine the director that a signal is coming from, and requires scanning in order to be used for imaging. Therefore, to localize the Bragg peak of the proton beam, multiple acoustic detectors are preferable.

According to certain aspects, the present disclosure provides a simulation workflow that models 3D protoacoustic imaging through a detector array using a clinical machine's logfile to generate the initial pressure, thereby enabling planning of protoacoustic imaging experiments. The present disclosure also analyzes the frequency characteristics of the resultant protoacoustic signal. The main constraints in deploying a multiple detector system for imaging of the proton beam dose deposition is frequency of the acoustic signal. As higher frequencies are associated with higher resolution, protoacoustic imaging resolution is determined by the highest detectable frequency in the signal. A proton beam pulse shape from a clinical proton machine is compared to that of x-ray linear accelerators (LINACs).

Theory of the Protoacoustic Effect

The protoacoustic effect is ultimately a thermoacoustic phenomenon, wherein incident pulsed proton radiation rapidly deposited energy inside the target tissue. This rapid deposition of energy results in a localized temperature gradient and subsequent thermoelastic expansion within the sample. As the target tissue relaxes, an acoustic wave is emitted, and propagates through the sample in three dimensions. A transducer (e.g. ultrasonic) can then easily be placed near the source on the surface of the tissue in order to image the proton energy deposition in the sample.

The governing wave equation of the induced protoacoustic signal is as follows $$\left(\nabla^2 - \frac{1}{v_s^2}\frac{\partial^2}{\partial t^2}\right)p(r,t) = -\frac{\beta}{x v_s^2}\frac{\partial T(r,t)}{\partial t^2} \tag{1}$$

Where $v_s$ is the speed of sound, p is the protoacoustic pressure, r is the position vector, t is time, β is the thermal coefficient of volume expansion, ℵ is the isothermal compressibility, and T is the temperature. This equation is commonly solved for a delta function excitation with a Green's function approach. Extension of the solution to a pulse of finite duration requires the convolution of the delta-function pulse solution with the pulse shape itself. Therefore, given the solution to an infinitely narrow pulse, $p_\delta$ the solution of the finitely large pulse is given as $$p(r,t) = \int_{-\infty}^{+\infty} dt' p_\delta(r, t-t')S(t') \tag{2}$$

where S(t) is the temporal pulse profile. Pulsed proton sources tend to have pulses on the order of μs in duration, which is not insignificant compared to the time taken by the sound to travel to a transducer some cm away (a transducer 7.5 cm away from the source will have a signal travel time of 50 μs. Therefore, delta function excitation assumptions are typically not valid for proton pulses in the range of tens of μs.

Equation 2 can be discritized for the purposes of dealing with digital signal. For brevity, let $D_{\delta i}$ be the discretized pressure vs. time signal of the ith element in the delta function simulation (with i ranging from 1 to 256, representing the number of transducers in the example of FIG. 1B).

A numerical convolution of a Gaussian pulse of variable pulse width with a detected acoustic pressure for all 256 sensor elements is performed. It begins by re-sampling/interpolating $D_{\delta i}$ to match the length of a discretized S(t), the re-sampling process being one of many potential processes known to those skilled in the art. The resulting waveform, $D_{Ti}$, represents the pressure that the sensor would detect in the case that the initial pressure was deposited over a finite time interval corresponding to a Gaussian pulse with width τ. Then, $$D_{\tau i}(k) = \sum_j D_{\delta i}(j)S(k-j+1) \tag{3}$$

where all functions are discretized. This can be turned into a function of time, $D_{\tau i}(t)$ by mapping the timestep vector to the elements within $D_{\tau i}(k)$.

It is important to note that equation 3 assumes that the transducer is a perfect broadband detector, thus idealized point detectors are considered for the remaining of the manuscript. If a more realistic detector is to be modelled accounting for potential bandwidth limitations of a transducer, then $D_{\tau i}$ must be filtered according to the transducer bandwidth. The simplest way to do this is to multiply by the transducer gain G(f) in frequency space.

The frequency of the protoacoustic signal is a crucial property for detection. So derivations are presented on how the pulse-width, shape, and transducer bandwidth is expected to influence the frequency spectrum of the generated signal. As real transducers are bandwidth limited, in experiment it is vital that the transducer bandwidth match the spectrum of the generated signal. For this a method is presented through which the expected spectrum of generated systems can be modelled prior to experiment, for both triangle and Gaussian pulses.

An intuitive way to understand the entire signal detection process is in Fourier space, as the convolution operater is equal to multiplication in Fourier space. Focussing in on a single detection element (a single transducer), here is outlined the theory behind signal detection. Let the detected signal by the single element be P, then the Fourier transform of this signal, $\hat{P}$, is given by $$\hat{P}(f)=\hat{S}(f)\hat{D}_{\delta}(f)G(f) \tag{4}$$

Where $D_\delta$ is the temporal impulse response of this element (this is the signal that would be detected if the pulse duration was infinitely short), and S is the temporal profile of the pulse. Here, the ^accent denotes a Fourier transform, and f is the frequency. G is the frequency dependent gain of the transducer. It should be noted that equation 4 consists first of the convolution operation in Fourier space (through the convolution theorem), followed by multiplication by the gain function of the transducer in Fourier space.

Through equation 4, all components of signal detection are incorporated into the final model. $\hat{D}_\delta(f)$ encodes information with regard to the geometry of the sample itself, G(f) encodes the transducers frequency response, and $\hat{S}(f)$ incorporates the pulse width dependence of the signal. It is important for all protoacoustic experimental planning to consider all aspects of equation 4, as this equation can ultimately guide transducer choice, proton beam choice, and object choice.

In equation 4, the only pulse width dependent multiplicand is $\hat{S}(f)$. And therefore the frequency dependence of pulse can be well understood through this function. Fortunately, $\hat{S}(f)$ is simply the Fourier transform of the temporal pulse profile, so can be easily extracted either analytically or numerically from various pulse shapes. For Gaussian pulses, extracted is the analytic form of $\hat{S}(f)$ for Triangle, Gaussian, and Trapezoidal pulses.

The Importance of Frequency

Ultimately the major governing factor in protoacoustic imaging resolution will be the final frequency spectrum of the final signal given in equation 4, which is the main topic of study in this paper. Here are presented various analyses of the protoacoustic frequency and its relation to pulse shape and image quality. It begins by presenting a simulation workflow for protoacoustic imaging. This workflow is then deployed to analyze the impact that protoacoustic pulse width can have on 3D image quality. Also examined us the impact of Signal-to-Noise ratio at single transducer elements on the final reconstructed image of the proton dose. Finally, an experimentally detected S(t) is collected and contrasted with signals of comparable time duration but different pulse shape.

Example System

An exemplary system associated with the present disclosure includes: A means for generating proton induced acoustic signals; An ultrasound transducer adapted to transmit ultrasound waves, receive ultrasound signal reflections from transmitted ultrasound waves, and receive proton induced acoustic signals generated from the proton source during proton therapy; A trigger sequencing logic device that tells the device to finish proton induced acoustic signal acquisition; and a protoacoustic imaging unit to receive and combine both protoacoustic imaging unit and ultrasound unit results and generate appropriate localization and dosing images after reconstruction.

In an exemplary system according to embodiments shown in FIG. 1A, the reflected ultrasound signal 108 is collected immediately after a firing trigger for proton beam 102. An ultrasound transducer 104 (e.g. an array such as that shown in FIG. 1B) is used to collect the protoacoustic waves 108. To compensate for relatively small proton induced acoustic signals, a multi-channel preamplification stage can be built used in a first stage of a proton induced acoustic imaging unit (not shown) coupled to transducer 108. After preamplification, the analog proton induced acoustic signals are acquired from transducer 108 and converted to digital signals, followed by an averaging/filtering stage. After averaging and filtering, the processed signal data can then be used for proton induced acoustic imaging reconstruction, such as the images shown in FIG. 1C. Those skilled in the art will understand many different processing systems and algorithms that can be used to implement such an imaging data acquisition processing unit that can be used in accordance with embodiments after being taught by the present examples.

The proton dose deposition can be reconstructed with protoacoustic imaging. After $D_{\tau i}(t)$ is obtained by convolution of a Gaussian pulse, the sensor positions in the simulation now serve as boundary conditions on which the boundary condition $P_i=D_{\tau i}(t)$ in time can be enforced, where $P_i$ is the pressure at the location of sensor i. The simulation is now run in reverse in time and the pressure is allowed to propagate. After the reverse simulation is run, the final pressure corresponds well to the initial pressure after a single iteration. The image reconstruction matches very well with the initial pressure. A 3D dose map can also be obtained in protoacoustic imaging with different view angles.

Example Methods

Figure 2:
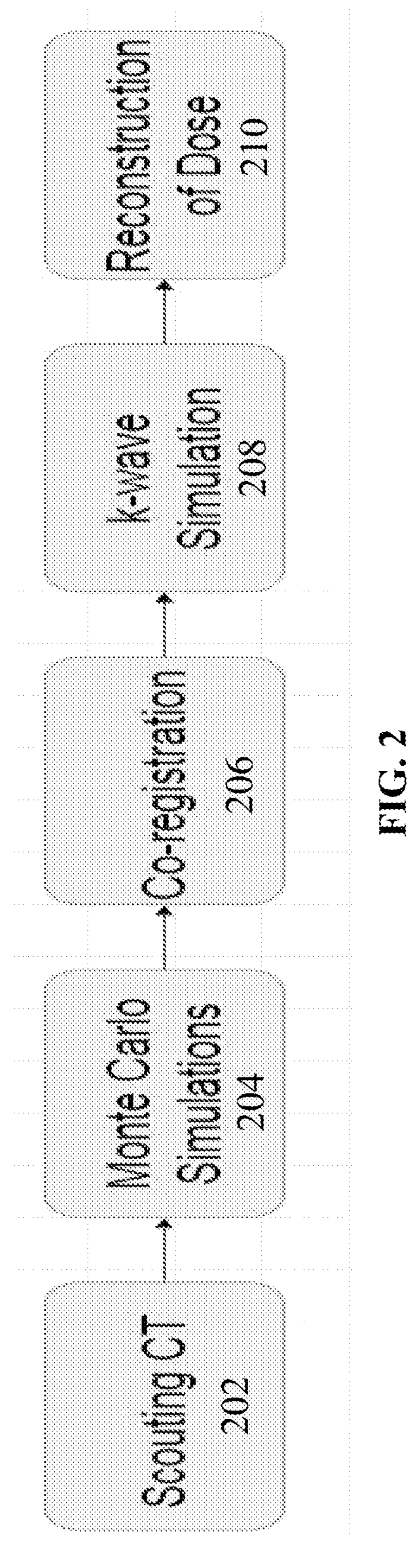
FIG. 2 is a functional block diagram illustrating an example protoacoustic imaging unit for protoacoustic imaging according to embodiments.

A formalism can be used through which protoacoustic signals can be characterized considering transducer bandwidth constraints as well as pulse duration of the incident radiation beam. Also included in some embodiments is a simulation workflow that is implemented in an example protoacoustic imaging system, a functional block diagram of which is shown in FIG. 2. This example workflow and imaging system includes using Monte Carlo simulations 204 for beam mapping on patient x-ray computed tomography (CT) 202. The simulation results from 204 are co-registered with the CT scan from 202, and the combined output is used as an input to k-wave simulations in 206 to model acoustic propagation. Also modelled is imaging using a 16×16 transducer array, possibly including 3D imaging. Lastly, simulated is the reconstruction procedure and reconstructing the initial dose is performed in 208. This workflow is deployed to analyze the impact that pulse duration and signal-to-noise ratio (SNR) has on the signal. Also collected is an experimental proton pulse signal from a Mevion S250 clinical machine to analyze using this formalism.

Figure 3:
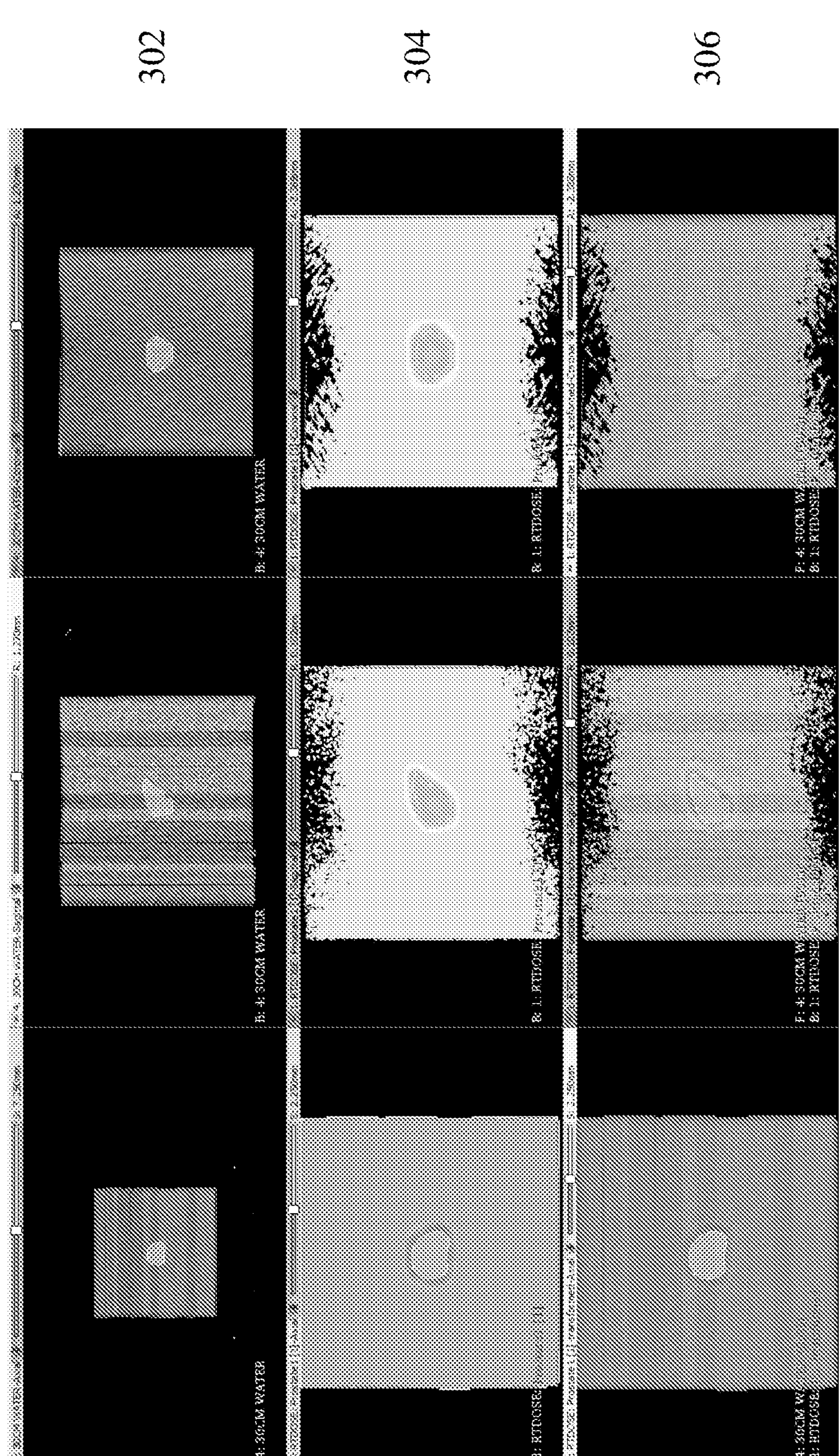
FIG. 3 provides graphs that illustrate aspects of an example Co-Registration of CT image with MC dose plan according to embodiments.

FIG. 3 illustrates aspects of Co-Registration of CT image with a MC dose plan according to embodiments, which can be implemented in the workflow and system shown in FIG. 2. The top row 302 shows a Phantom CT overlaid with a digital prostate phantom (blue). The middle row 304 shows a Proton Dose overlaid with a digital prostate phantom (blue). The bottom row 306 shows a Co-registered image with Phantom CT and prostate dose using feature mapping of the digital prostate phantom.

Example Results

It was found that the simulation workflow implemented as shown in FIG. 2 can flexibly model proton acoustic imaging. It was also found that changing the pulse width can heavily impact resolution of the reconstructed image. An SNR analysis showed that proton-acoustic image reconstruction is possible even when the noise amplitude is larger than the signal amplitude on individual transducers, an interesting result due to averaging from the time reversal reconstruction algorithm. It is found that a 4 μs Gaussian proton pulse can theoretically generate a signal in the range of MHz so long as the spatial heating function has sufficiently high temperature gradients. It is additionally shown that this is also the case when the pulse shape is trapezoidal. However, it is noted that the condition of spatial gradients allowing for MHz frequency generation is not typically the case in clinical settings with either pulse shape. Array simulations show that high-resolution dose maps in 3D can be retrieved with a 2D matrix (16×16 elements) array.

Example Conclusions

The results shed light on the frequency properties of protoacoustic emissions and how they may be characterized in the future. The formalism also predicts that if low-pulse durations are a technical constraints of accelerator construction, then higher frequency generation is still possible if care is taken to maximize dose gradients in the sample (e.g. via the use of absorbers). The reconstruction results also show that photoacoustic imaging is possible using arrays, even when single elements have SNR of <1, due to averaging effects of the reconstruction algorithm. It is also shown that proton pulses signals lasting several us can still potentially generate protoacoustic signals with higher frequencies (MHz) than previously thought, thereby allowing for high-resolution protoacoustic imaging.

Monte Carlo Simulations

The present Applicant designed and deployed a five stage protoacoustic imaging system and workflow in order to achieve realistic protoacoustic simulations in line with clinical parameters in accordance with the example of FIG. 2. The first stage in 202 is to conduct a scouting CT of the sample in question. For convenience, this is done with a 30 cm×30 cm×30 cm solid water phantom which is a homogenous target. This is done to obtain QA measurements and then the logfile is used to compensate for delivery uncertainties (spot MU, spot position and AA positions). The CT is merged with a realistic human body structure set, featuring a prostate, rectum, and bladder and their respective positions. A standard two fields spot scanning proton treatment plan can be generated to target the prostate as the main tumor site (Field one: 13 layers/438 spots. Field two: 13 layers/456 spots. 2 Gy/fraction. Maximum MU per spot: 8.2746 MU. Minimum MU per spot: 0.2612 MU). After the plan was delivered on a Mevion S250i proton system, the system logfile can be captured and converted into simulation ready text file with in house tools.

With a completed beam line components model, a TOPAS Monte Carlo (MC) simulation in a next stage 204 can then be run on the Water phantom corresponding to machine delivery parameters including real time spots positions, spot MU values and Adpative aperture leaf positions.

Co-Registration

The TOPAS simulation is run on a small part of the water phantom with different spacing than the original CT. This is for the purpose of saving computation time. Therefore to run k-wave simulations on the resulting dose, the dose is preferably co-registered with the scouting CT prior to k-wave simulation in a stage 206. The dose output of the MC simulation is overlaid with the solid water phantom CT via feature based co-registration in a 3D slicer. The result of the co-registration is shown in FIG. 3. A 3D structure set of organs was overlaid on both the dose output of MC simulations and the 3D solid water phantom. The two images were then co-registered via the use of this common structure of prostate.

K-Wave Forward Simulation

Following the MC simulations of the proton dose, the dose is imported into MATLAB using the function dicomread. Here, the 3D dose can be used as a 3D initial condition to equation 1 using the k-wave MATLAB toolbox in stage 208. As the dose is linearly proportional to the protoacoustic initial pressure, this linearity be used to generate relative protoacoustic pressure maps in MATLAB. This simulation is modelling a delta function pulse in order to obtain an estimate of $p_\delta$. After initialization, the pressure is then allowed to propagate throughout the sample using a pseudospectral solution method. For speed, the code is run using the C++ version of k-wave as opposed to running the simulations in MATLAB.

It is important to note, however, that protoacoustic imaging of the Mevion S250i would not image the entire dose deposited, only individual shots of the proton beam. Therefore, for this machine, protoacoustic imaging can only image single shot dose deposition at once. However, the sum of images of all shots can be overlaid following proton emission, thereby allowing protoacoustic imaging to reconstruct the total dose deposited. In this paper, we proceed assuming that an equivalent procedure can be suitably modelled by simulating the cumulative dose as a full dose deposited at once. It is believed that this is a valid assumption as the cumulative protoacoustic pressure of all shots will itself be proportional to the cumulative dose, thus requiring only the addition of reconstruction pressure from single shots.

A sensor array matching the dimensions of a parallel receiving transducer element can also be added to the simulation in order to simulate signal reception by an ultrasound transducer array. The sensor array consists of a 5×5 cm planar array with 16 elements evenly spaced in each direction. These dimensions were chosen to match a planar array that is actively used in experiments. The sensor array was placed to match the plane at z=−150 mm.

Noise Analysis

White noise with maximun amplitude equivalent to the maximum point of the signal was generated using a random generating function. This noise was then scaled and added to the detected signal prior to reconstruction. The effect of varying Signal-to-Noise-Ratios (SNRs) on image reconstruction was investigated.

Reconstruction

The final stage in the simulation workflow example of FIG. 2 is the reconstruction of the dose via a time reversal algorithm in stage 210, which is conveniently built into the k-wave toolbox. This is done through the reconstruction of the initial pressure in the k-wave simulation. After Du (t) is obtained by convolution of a Gaussian pulse, the sensor positions in the simulation now serve as boundary conditions on which the boundary condition $$P_i=D_{\tau i}(t)$$

in time can be enforced, where $P_i$ is the pressure at the location of sensor i. The simulation is now run in reverse in time and the pressure is allowed to propagate. After the reverse simulation is run, the final pressure corresponds well to the initial pressure after a single iteration.

One consideration that must be made is the avoidance of the inverse-crime in numerical reconstruction, in order to account for this fact the reverse simulation is performed in a slightly different number of grid points than the forward simulation.

Quality of Reconstruction

A qualitative metric to quantify the quality of the reconstruction is required to properly evaluate the success of the reconstruction. For this particular set of simulation experiments, the square mean difference between the initial pressure and the reconstruction was used as the metric to evaluate the quality of the simulation.

Single Dose Experiment

An experiment using a single dose shot was performed and used as input to create a simulation and reconstruction with transducers at different distances from the Bragg peak. This allows to explore the type and frequency that the transducers are going to detect at those locations. The transducers were spaced out on the lateral direction by 46 mm and in the axial direction by 50 mm.

Active proton pulse signals were monitored with a Beam Exit Quadrant Foil Chamber (BEQ) immediately placed at the exit port of cylcotron. A Faraday cup, in house built according to design of Cascio and Gottschalk together with a high speed current amplifier (HCA-4M-500K, FEMTO, Germany) was mounted on the gantry nozzle at vault isocenter to measured the single proton pulse width and charge.

Figures 4A, 4B, 4C, 4D, 4E:
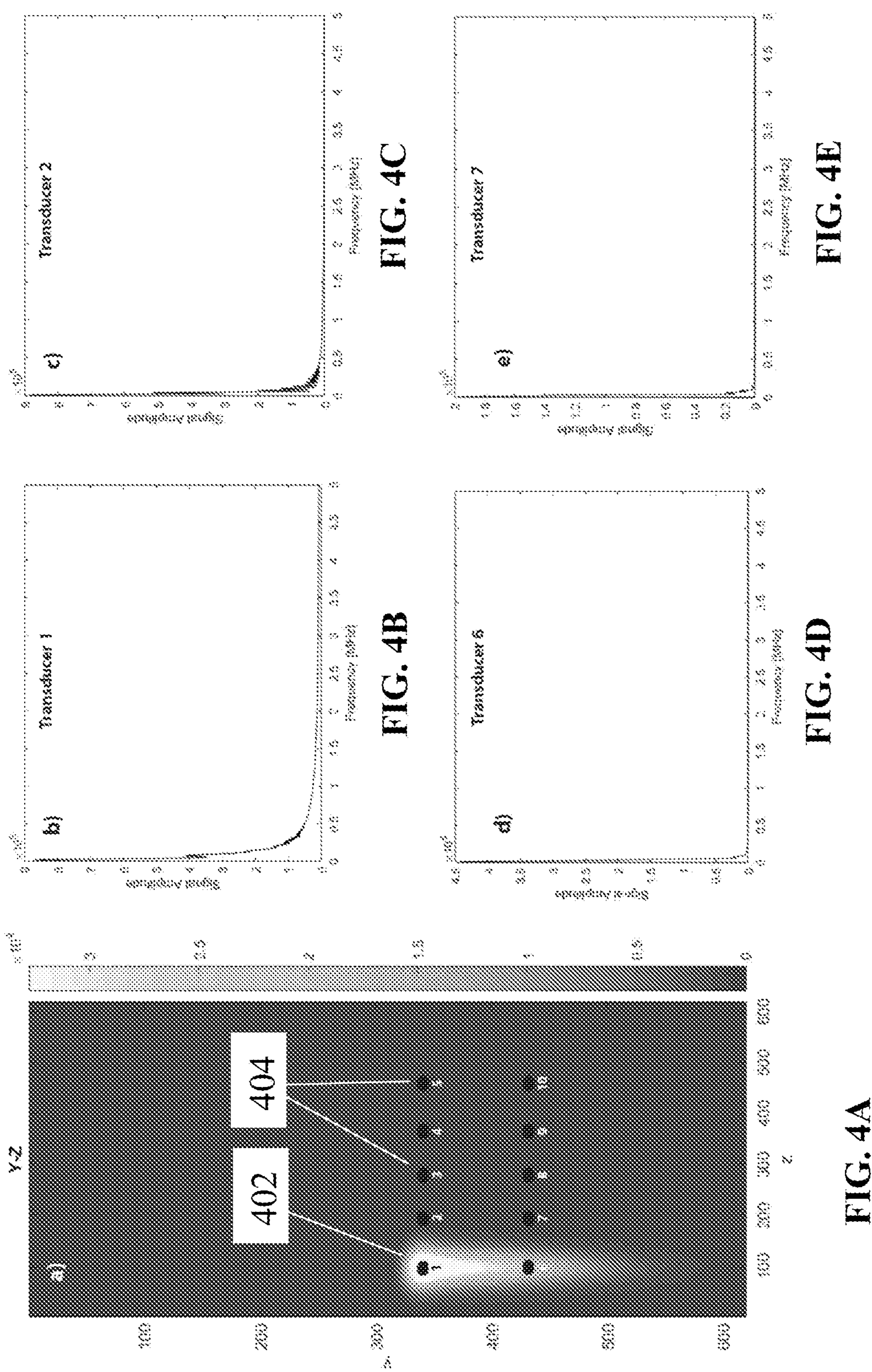
FIGS. 4A to 4E are diagrams illustrating an example Single Dose Shot experiment with transducers at different positions.

In order to understand the spatial heating function, a forward simulation was carried out for a single spot dose such as that illustrated in FIG. 4A. Here, some important characteristics of the spatial heating function can be visualized. This simulation consists of a spot dose 402 along with some idealized transducers 404 (unlimited bandwidth and perfect sensitivity). While transducer 1 shown in FIG. 4B (directly on the Bragg peak) does detect some frequencies in MHz, they quickly decay by the time the pulse arrives at transducer 2 (5 cm away), as shown in FIG. 4C. However, it can be seen upon close visual inspection of the waveform from transducer 2 that there is still a non-zero (albeit extremely weak) contribution of a 1 MHz signal at this distance from the beam.

Figures 5A, 5B:
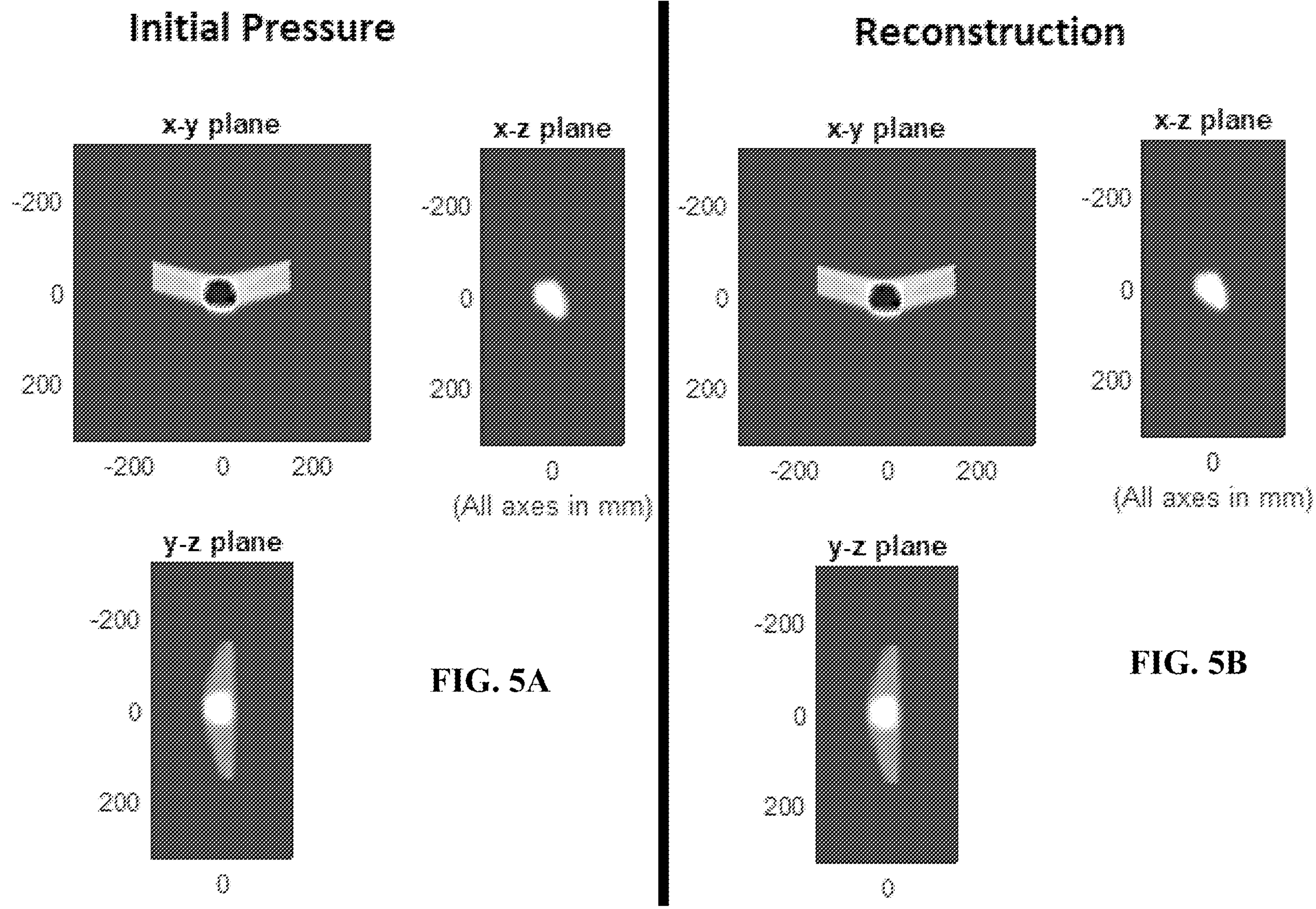
FIGS. 5A and 5B are diagrams illustrating example Initial (FIG. 5A) and Reconstructed (FIG. 5B) Pressures for a simulated proton source using imaging techniques in accordance with embodiments.
Figures 6A, 6B, 6C, 6D, 6E, 6F:
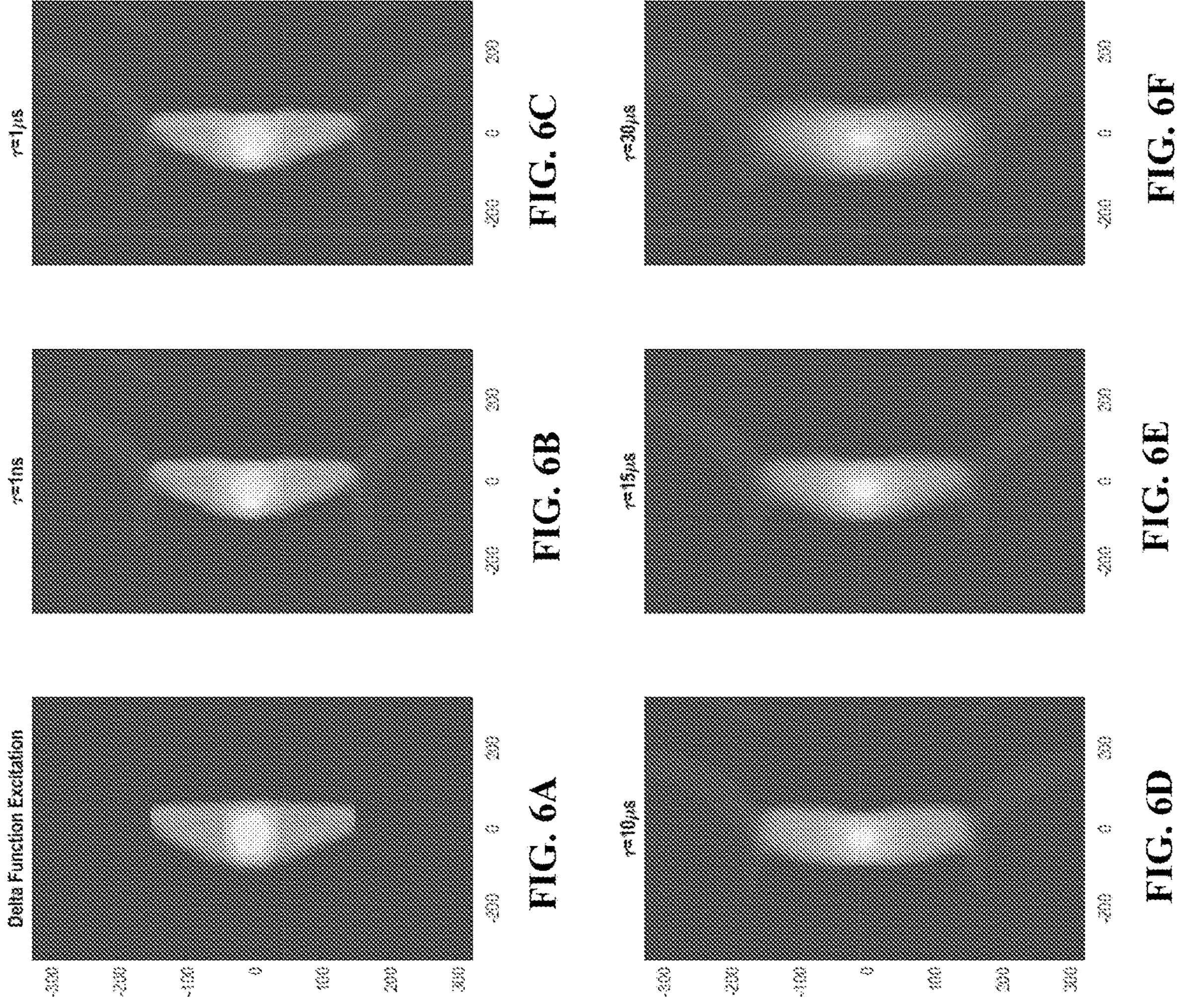
FIGS. 6A to 6F are diagrams illustrating pulse width dependence on Bragg peak Localization. All axes in mm.

Following on the spot dose simulation, also run were protoacoustic simulations of the overall dose delivered (which would be the cumulative result of individual spot doses). This was for the purpose of examining the impact of the pulse width on the signal. Reconstructions were run for a variety of protoacoustic pulse widths, specifically at $\tau$=1 ns (to test the convolution script), 1 μs, 10 μs, 15 μs, and 30 μs. An example output (with $\tau$=1 μs) is shown in FIG. 5B. It can be seen that at this pulse width, while there are some artifacts present, the pressure can be reconstructed from the initial input shown in FIG. 5A with relatively good fidelity.

The performance of the reconstruction, as expected, decays with increasing pulse width. The pulse width dependence on the reconstruction is shown in FIGS. 6A to 6F. As the timestep for the delta function simulation is only ~0.25 μs, the simulation where $\tau$=1 ns is exactly identical to the delta function reconstruction. Nevertheless it was chosen to include it in FIG. 6B as it confirms that the numerical convolution script works as intended. It can be seen that at very low pulse widths (e.g 1 us in FIG. 6C vs. 10 us, 15 us and 30 us in FIGS. 6D to 6F respectively) the reconstruction performs best. This is because at these pulse widths $$\sum_j D_{\delta i}(j)S(k-j+1) \approx D_{\delta i}(k),$$

and the convolution function does not change the characteristics of the signal all that much. This is consistent with what has been reported in literature.

Furthermore, as set forth in the Table below, the mean square difference between the initial pressure and the reconstruction shown an increase with increasing pulse width. These results support the trend previously described where the performance and quality of the reconstruction decay with increasing pulse width.

Table 1: Mean Square Differences between the initial pressure and the reconstruction.

| Mean Square Difference | |
|---|---|
| 1 nsPulse | 2.60E−04 |
| 1 usPulse | 2.60E−04 |
| 10 usPulse | 2.97E−04 |
| 15 usPulse | 3.32E−04 |
| 30 usPulse | 6.46E−04 |

The condition of stress confinement on pulse width is given as $$\tau < d_c/v_s$$

Where $d_c$ is the desired resolution. As this simulation operates in a discretized space, the maximum achievable resolution in the simulation is limited by the grid spacing, which matches the dimensions of the planning CT scan (1.3 mm in x and y directions, 2.5 mm in the z direction). This corresponds to a stress confinement time of 8.66 μs in water. Therefore, stress confinement at this length scale is met for all simulations of $\tau$<8.66 μs.

The effect of stress confinement can be seen in FIGS. 6A to 6F. For all the reconstructions without stress confinement, there is little to no difference seen. This is because all of these conditions are well approximated as delta pulse excitations at the resolution limits set by the planning CTs. However, once stress confinement starts to be breached at the planning CT resolutions, resolution decay in the Bragg peak reconstruction is visible. These simulations demonstrate a useful guideline in clinical procedure of determining the optimal proton pulse peak for the desired accuracy of Bragg peak localization. The dose deposited can also be rendered in 3D using rendering software such as AMIRA.

Figures 7A, 7B, 7C, 7D, 7E, 7F:
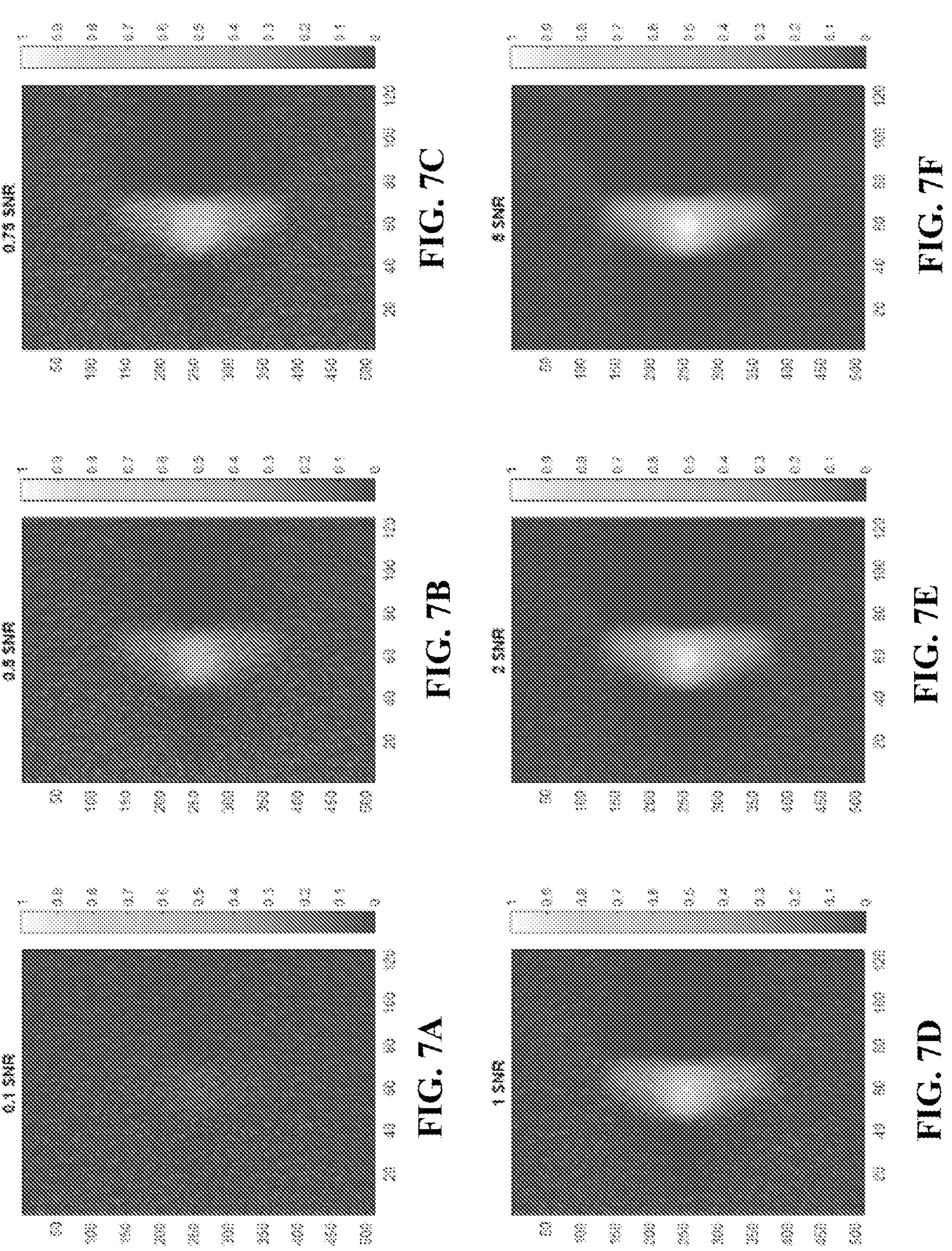
FIGS. 7A to 7F are diagrams illustrating example effect of SNR on image reconstruction for a pulse with of 15 μs according to embodiments. All axes in mm.

The effect of varying the SNR on signal reconstruction when $\tau$=15 μs can be seen in FIG. 7A. As expected, poorer SNRs results in poorer reconstruction of the initial dose (e.g. 0.1 SNR to 0.7 SNR as shown in FIGS. 7A to 7C, respectively), with an SNR of 5 very accurately reproducing the initial pressure as shown in FIG. 7F. However, it can be seen that even when the amplitude of Noise is higher than the amplitude of the signal (SNR<1), the dose deposition can be partially made out, albeit with low resolution. The reason that the reconstruction algorithm can still reconstruct something despite the noise being stronger than the signal, is that the time-reversal procedure maps the detected signal at all transducers back towards the source. Therefore, across all transducers which now act as emitters during time reversal, there is an 'averaging' effect that occurs because noise from various transducers is send back into the sample geometry. As the noise from different transducers gets averaged out, some of the original dose still appears even with an SNR of <1. This bodes well for experimental set-ups as it implies that, if SNR at a single element is <1, running the reconstruction algorithm may still reveal useful information about the dose distribution.

DISCUSSION

The simulation and protoacoustic imaging workflow demonstrated in this study provides a road-map through which clinicians can assess the feasibility of protoacoustic range verification for a wide variety of proton Bragg peaks. The simulation workflow is versatile with the planning CT used, the pulse width of the generated proton beam, the detector distribution, the size of the simulation region, and sound speed. This reconstruction is also robust to heterogeneities in sound speed in the sample, as the time reversed simulation is run with the same grid that ran the forward simulation, therefore if the planning CT can map tissue sound speeds and densities, this is a usable workflow for clinical practice.

It is also shown that reconstruction of the dose is possible even in the situation where individual element SNR is <1, due to the averaging effects of the time-reversal algorithm. This is particularly interesting from an experimental standpoint as it implies that imaging with an array and reconstructing can benefit from unique advantages of time reversal 'averaging' effects. That being said, single pulse measurements will almost certainly not be detectable with SNR<1, and will require many averages as is typical in protoacoustic experiments to achieve SNR>1 in a single element. Therefore, it is crucially important to emphasize that while 'averaging' effects from time reversal enable some image reconstruction when single element signals are <1, it will still likely be important to perform multiple averages over single elements.

Simulation results show that protoacoustic Bragg peak localization is possible in 3D with a 2D matrix ultrasound array, and therefore that full relative dose reconstruction (i.e. an image where the brightest pixel is the maximum initial pressure) is possible using protoacoustic Bragg peak range verification.

A simulated 3D dose map of the proton beam with protoacoustic imaging with a 2D matrix ultrasound array is obtained. This can overcome the challenge of using a point-detector which requires raster scanning to generate images. Theoretically, the Bragg peak can not be localized with single acoustic detector. To pinpoint the exact localize of the point protoacoustic source, a minimal of three detectors is needed. For high-resolution clinical imaging however, many more detectors are needed.

Additionally, the speed of the simulation can be improved upon via the use of parallel processing techniques. Currently forward and reverse simulations are run on a conventional dual core desktop computer, which can limit the time of the simulations to several hours. However, through parallelization of the Fourier transform step used in k-wave's pseudospectral method, the speed of simulations can be drastically improved roughly linearly with the number of cores available.

There are some important limitations of this approach that should be mentioned. Specifically, the simulation only uses point sensors and so does not simulate the effect of sensors themselves having some size. The simulation also assumes a uniform water medium, which can approximate tissue but is not the same as using soft tissue medium which could change propagation parameters. Additionally, heterogeneities have not currently been studied. It is believed that a combination approach which considers 3D tissue heterogeneities while simultaneously using clinical logfiles on heterogeneous tissue phantoms would be the most accurate possible way to conduct protoacoustic simulations and propose this as a goal for future study. It is also noted that not explicitly modelled is the impact of transducer bandwidth on the final reconstruction, and it is assumed perfect bandwidth. This so that the impact of the pulse width could be analyzed independently, though future studies can perform a similar study on bandwidth by bandpass filtering prior to time reversal reconstruction.

It should also be noted that the reconstruction accuracy can be affected if acoustic properties of the sample change change (due to breathing) and heterogeneities play a large role in signal scattering. Therefore ideal deployment of this method would be either coupled with patient breath hold or deployed in areas that are mostly static during patient breathing.

To examine the effect of pulse width on frequency, considered is an experimental S(t) obtained from a clinical proton machine. FIG. 8A shows the signal recorded with a BEQ chamber in low temporal resolution, with multiple pulses (spikes) present. At this level the overall pulsing behavior of the proton machine can be seen but individual pulses width cannot be accurately made out due to slow electronics. FIG. 8B shows a zoomed in version of the pulses, recorded with a Faraday cup with a high speed Amp so as to show the pulse shape. It can be seen from FIG. 8B that the shape of the beam is roughly that of a skewed Gaussian, as is also common in photoacoustic context. Therefore a Gaussian is fit to the curve and taken its analytic Fourier Transform, shown in FIG. 8C. Interestingly, it can be seen that the maximum frequency present in this signal is well in the range of MHz, yet us pulses from clinical linear accelerators do not usually generate signals in the MHz range. This implies that the major roadblock for high frequency generation in proton-acoustics is more spatial than temporal, as a comparison between FIG. 8 and FIG. 4 shows that by far the bottleneck of low frequency is in the spatial heating function of the proton beam as opposed to the pulse shape.

This figure, taken with the result from the spot dose, reinforces that while pulse width is an important factor for thermoacoustic generation, it is not the only factor to consider. Ultimately the driving function in equation 1 is the derivative of the temperature rise. Therefore, a pulse with a sufficiently quick rise time, even if total duration is long, should also be able to generate thermoacoustic signals at higher frequencies. This is illustrated in FIG. 9, where a trapezoidal signal is examined with 4 μs pulse duration and 125 ns rise time. This signal shape is chosen to match those typically observed in clinical LINACs. It can be seen that the Fourier transform of such a pulse still contains significant frequency contributions in the MHz range, as is the case for a Gaussian μs pulse examined above.

The present Applicant has simulated the Gain function, G(f), of a transducer with a flat passband of 1-4 MHz, and it can be seen from the product of the G(f) and S(f) that the final signal (prior to convolution with $D_{\delta as}$ in equation 4) has significant frequency contributions in the MHz range. Therefore, even signals with several us duration can be engineered in such a way that they can generate high-frequency signals in the MHz range. Such frequency ranges are much more suitable for high-resolution protoacoustic imaging than those typically observed from clinical machines as measured in FIGS. 7A to 7F, and so the spatial heating function again is the main bottleneck. Therefore, this work, combined with the results in FIGS. 6A to 6F, implies heavily that there is a distinct benefit in the context of protoacoustic imaging towards making spatial gradients as sharp as possible in protoacoustic imaging (e.g. with some artificial absorber or contrast agent present), as this has the potential to yield much higher frequencies than are typically observed in thermoacoustic clinical experiments.

It additionally implies that whereas historically it has been assumed that clinical radiation sources with μs pulse durations will only generate frequencies in the kHz range, it is possible to generate MHz signals from μs pulses as well if the spatial gradients from the beam are sufficiently sharp. An interesting consequence of this exercise is that we have a plausible explanation for why us pulse trains, as are common in conventional x-ray LINACs, may actually generate thermoacoustic signals that are of higher frequency than expected. Essentially, as LINACs use a pulse train with a trapezoidal envelope, the most rapid change in S(t) occurs at the rise and fall, therefore a trapezoidal signal with rise time in the range of ns can in theory produce a thermoacoustic signal that is in the MHz range. This can serve to explain why other studies have observed signals in the MHz range despite using beams with pulse durations in the range of several μs. The underlying implication of this is that if the rise time of a source is sufficiently sharp then this can potentially produce high frequency signals even if the total pulse duration is longer.

A theoretical analysis of the proton frequency can provide a road map to clinicians interested in conducting protoacoustic experiments. A crucial experimental consideration in thermoacoustics is the expected frequency spectrum of the detected signal. This is a key factor in choosing appropriate detection equipment with appropriate bandwidth. Using this workflow, protoacoustic experiments can be planned such that the bandwidths of detecting transducer overlaps well with the frequencies present in the signal, incorporating both the geometric characteristics of the sample as well as the temporal characteristics of the radiation excitation.

Additional Observations and Embodiments

As set forth above, while the experimental observation of acoustic waves induced by a proton beam from a patient was first reported in 1995, there has been renewed interest in this technique over the last few years due to upgraded proton machines and ultrasound detectors. Unlike PGD and PET, which require bulky and expensive gamma-ray detectors around patients, protoacoustic detection systems comprise of a single detector or an array of ultrasound detectors, which only require a small space and are more affordable. Recently, including the foregoing, many studies have been conducted to reduce the range uncertainty during proton therapy by exploiting protoacoustics. These experiments were performed using a linac, synchrotron, cyclotron, and isochronous cyclotron, all with encouraging results. Moreover, the protoacoustic image can be a perfectly co-registered overlay of the Bragg peak onto an ultrasound image. These latest studies demonstrated the feasibility of using protoacoustic imaging as a viable range verification technique in a clinical radiotherapy environment. However, the real clinical application has been hampered by the weak protoacoustic signal. In return, the dose sensitivity is low (>10 Gy), and more than 1000 averages were needed to obtain a reasonable signal-to-noise ratio for protoacoustic signals, which renders the real-time localizing the Bragg peak during proton therapy virtually impossible.

Figures 10A, 10B, 10C, 10D:
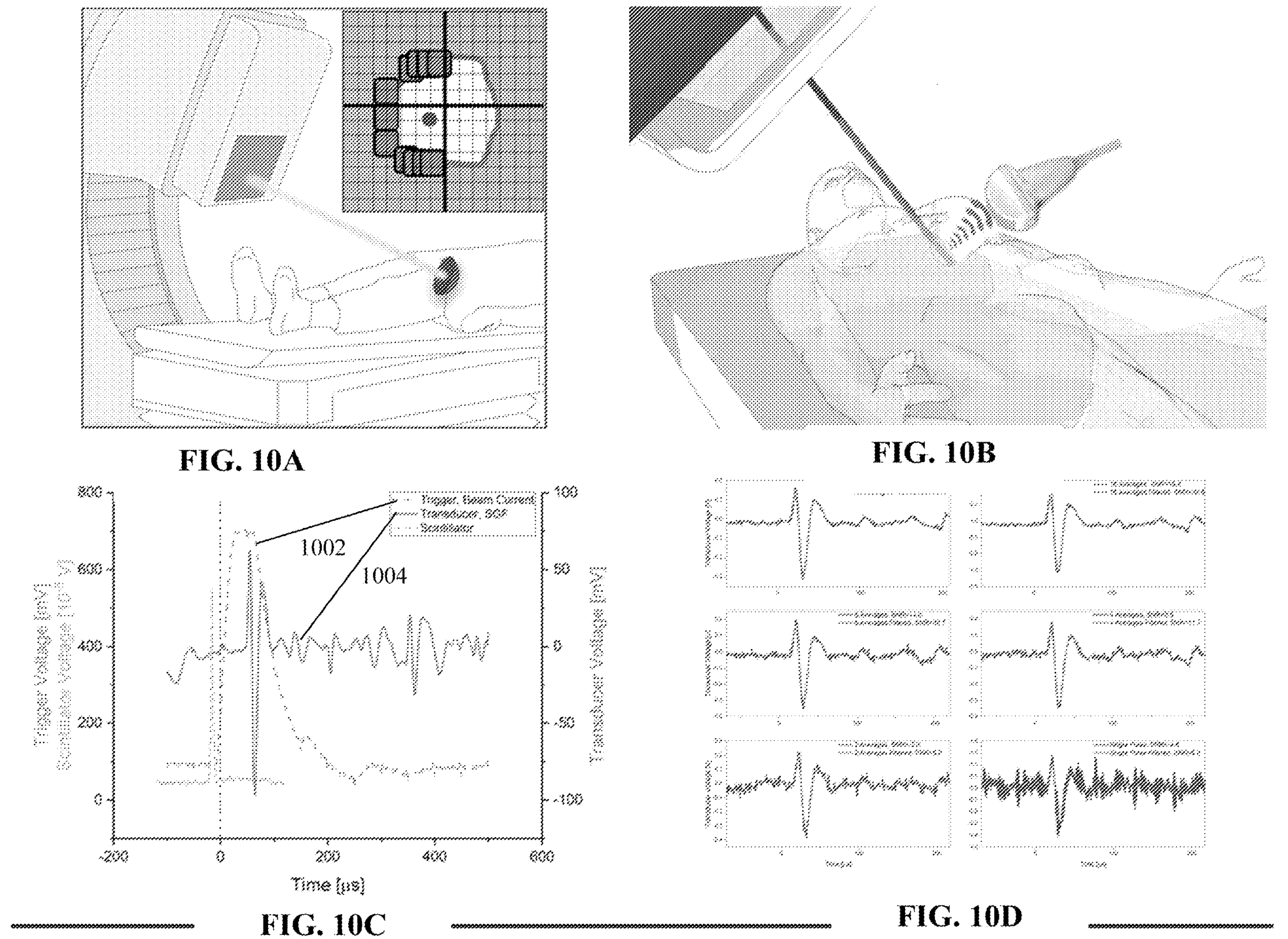
FIGS. 10A to 10D are diagrams illustrating additional aspects of embodiments.

In the above and foregoing embodiments, methods and apparatuses are provided to use precision-guided protons for cancer therapy, enabled by a protoacoustic system such as that shown in FIGS. 10A and 10B, which can: 1) monitor the position of the Bragg peak, and 2) quantify the radiation dose in tumor in real time. The feasibility of protoacoustic detection as an in vivo method for measuring the range of proton dose depositions during patient treatments was investigated by measuring proton dose depositions across the entire energy range of a clinical proton system utilized in patient treatments with single pulse signal acquisitions from a transducer. With generated protoacoustic signals 1004, the utilization of a trigger signal 1002 from the proton system shown in FIG. 10C, and the application of a Savitzky-Golay digital filter, an appreciable signal-to-noise ratio (SNR) is obtained for single pulse signals that demonstrates promise for clinical implementation, as shown in FIG. 10D.

In pulsed radiation therapy, a pressure wave is induced in the medium due to the deposited dose, or deposited energy, causing microscopic thermal expansion if the excitation pulse is small enough (on the order of microseconds). This generation and propagation of the acoustic signal (in this case, protoacoustic) under the assumptions of thermal confinement and negligible acoustic attenuation can be expressed as:

$$\left(\nabla^2 - \frac{1}{c^2}\frac{\partial^2}{\partial t^2}\right)p(\vec{r}, t) = -\frac{\beta}{C_p}\frac{\partial H(\vec{r}, t)}{\partial t}$$

where $p(\vec{r}, t)$ denotes the acoustic pressure at location $\vec{r}$ and time t, c is the speed of sound, β is the thermal expansion coefficient, $C_p$ is the target's heat capacity at a constant pressure, and $H(\vec{r}, t)$ is the heating function which can be decomposed into separate spatial and temporal functions as $H(\vec{r}, t)=E(\vec{r})F(t)$, with $E(\vec{r})$ and F(t) being the proton energy deposition in the tissue and temporal proton pulse[x].

The solution to Eq. (1) due to delta pulse excitation ($F(t)\approx\delta(t)$) is given as:

$$p_G(\vec{r}, t) = \frac{\beta}{4\pi C_p}\frac{\partial}{\partial t}\left(\frac{1}{ct}\int_{S(\vec{r},t)} H(\vec{r}')dS'(t)\right); \left|\vec{r} - \vec{r}'\right| = vt,$$

where S'(t) denotes a time-dependent spherical surface centered at the detector location $\vec{r}$ such that $|\vec{r}-\vec{r}'|=ct)$[x]. The protoacoustic signal generated due to a proton pulse function F (t) will be:

$$p(\vec{r}, t) = F(t) * p_G(\vec{r}, t)$$

The finite temporal width of the proton pulse leads to the widening of the protoacoustic signals. In protoacoustics, protons cause an abrupt temperature rise at the location of deposition. Due to the unique nature of the Brag peak, protons that are deposited in the pre-Bragg peak region will emit a cylindrical pressure wave from the axis of deposition whereas the protons deposited in the Bragg peak region emit a spherical pressure wave that mainly propagates distal to the Bragg peak along the axis of deposition. These waves are denoted as the α wave and the γ wave, respectively. The wave of interest in this work is the γ wave. Assuming negligible noise contribution, the time-of-flight calculation for the γ wave when the detector is placed distal to the Bragg peak on the beam axis can be determined by:

$$\tau = \frac{l}{c}$$

where τ is the arrival time, c is the speed of sound in the medium, and/is the on-axis distance of the detector surface from the Bragg peak. The ideal arrival time can be meaningfully linked back to the Bragg peak location. The arrival times are measured am compared from both the simulation and experiment.

In order to measure the Bragg peak localization for utilization in patient treatments, an experiment was designed and executed. Beam energies ranging from 45.5 MeV to 227.15 MeV, in approximately 20 MeV increments, were delivered with various amounts of signal averaging. Five signals were acquired per beam depth used and the mean range depth of these signals was calculated. Three data sets were gathered to investigate the accuracy of this method with various charge-per-pulse depositions. With the smallest single deposition of charge in patient treatments being 4 pC, data sets contained 1024 average signals with 3 pC/pulse, 4 average signals with 4 pC/pulse, and single pulse signals with 7 pC/pulse. The energy-range relationship of the protoacoustic results were compared to that of the ionization depth-dose (IDD) of the proton system taken from commissioning, which utilizes an ion chamber in (FIG. 11A). Signals of 1024 averages had all energies within approximately 0.5 mm of the ion chamber data (FIG. 11B). The standard error in these measurements were calculated to be approximately 0.1 mm. Some data points have a standard error of 0 mm, since the range depth was calculated to be the same for all five acquisitions for that energy. Signals of 4 averages were measured to be within approximately 1 mm of the ion chamber data (FIG. 11C). The standard error was calculated to have increased slightly with increasing distance from the transducer, with the maximum standard error of approximately 1.3 mm. Single-pulse signals were measured to be within 1 mm of the ion chamber data (FIG. 11D). The maximum standard error was calculated to be approximately 0.7 mm. At least 7 pC/pulse was necessary to obtain submillimeter results with single pulse due to substantial noise contributions.

The previous data with promising single pulse results was supported by further altering the range in 2 mm steps, which is the smallest alteration possible with the proton system. With a 2 mm shift in water corresponding to approximately 1.3 μs, and the sampling time of the signals being 0.5 μs, this shift is decipherable in the displayed signals with a separation of 1.5 μs (FIG. 12A).

For the single-pulse acquisitions, the mechanics of proton bunch delivery was slightly altered in the proton system to obtain the submillimeter results. These mechanics are in place for comprehensive patient safety and more accurate charge delivery in patient treatments since beam deliverance can vary by approximately 20%. Normally, the proton bunch is delivered in 4 packages with the first being around 80% of the total charge mentioned. The next three would be divided across the final 20% in the charge delivery. This created some inadequate results with single pulse acquisitions since it was uncertain which package was being collected in signal acquisitions, resulting in various levels of signal amplitude. The settings were changed for the single-pulse acquisitions to have all 100% of the charge delivered in 1 package to have a more certain knowledge of the charge delivery.

The dependence of the range variations and signal voltage on the charge deposition was investigated by acquiring various charge-per-pulse depositions that varied from 2 pC/pulse to 9 pC/pulse from single pulse signals. A beam energy of 162.78 MeV, which correlates to approximately 18 cm, was delivered with the transducer placed at a depth distance of 28 cm. Five sets of signals were acquired per charge deposition. The detected range variations of the fixed-energy single pulse protoacoustic signals from the corresponding IDD were measured (FIG. 12B). All mean measurements for the various charge depositions were measured to be within approximately 1.3 mm of the IDD, with the higher depositions being more accurate. The largest standard deviation recorded was approximately 0.8 mm, resulting from a 3 pC deposition. A qualitative assessment shows that higher charge depositions are more robust, supplementing the range verification results.

The peak-to-peak voltage of the various signals were also measured, and the mean and standard deviation were then calculated for each charge deposition set (FIG. 12C). The data was then fit with a linear curve and was calculated to have an R-squared value of 0.994, implying a good fit. This dosimetric data implies that there is a linear relationship between the charge delivered and the amplitude of the signal, meaning that there is a relative means of assessing the deposited dose in the medium by relating this to the deposited charge.

The feasibility of protoacoustic detection as an in vivo method for measuring the range of proton dose depositions during patient treatments was investigated by measuring proton dose depositions across the entire energy range of a clinical synchrocyclotron utilized in patient treatments with single pulse signal acquisitions from a transducer. The energy-range relationship developed from the protoacoustic signals were compared to that of an ion chamber measuring the ionization depth-dose. With single pulse acquisitions having sub-millimeter range variations, protoacoustic detection is proven to be a viable in vivo method for measuring proton dose depositions with high precision during patient treatments. This method preserves advantages for clinical applications, being the potential for real-time acquisitions, high SNR, high spatial resolution, and simple, low-cost equipment. This method can therefore be implemented into the clinical workflow for pre-treatment, treatment, and post-treatment purposes of both range and dosimetric verification with the potential for adaptive planning.

Figure 13:
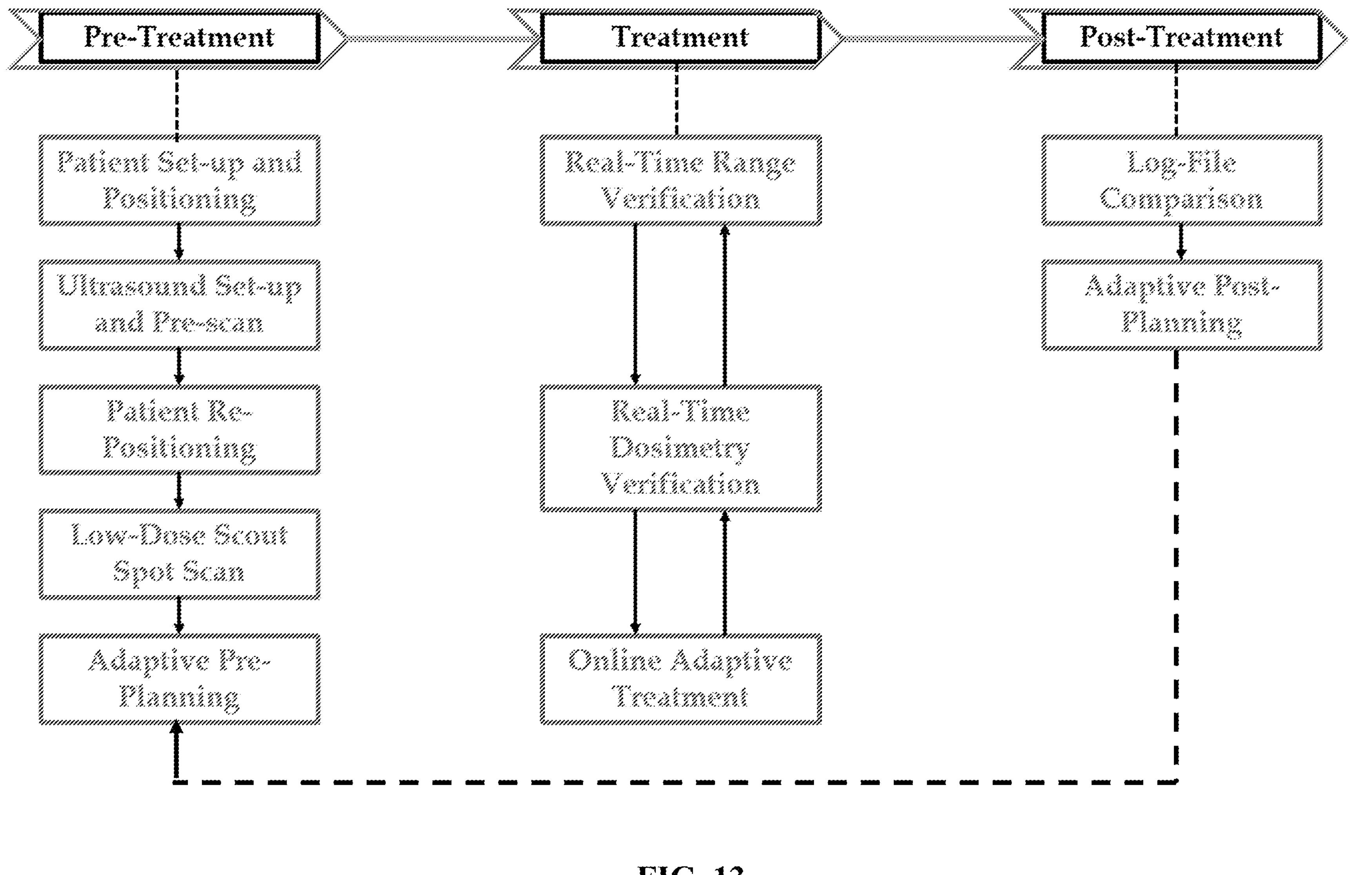
FIG. 13 is a flow diagram an example workflow in accordance with additional embodiments.

If results continue to improve over the years, this technique could be directly implemented into the clinical workflow (e.g. the workflow shown in FIG. 13). By placing the transducer on the body of the patient with ultrasound gel applied, there can be a method for verification of patient set-up and positioning that does not involve ionizing radiation. This can be done with the transducer operating in a transmit and receive mode like a typical ultrasound procedure to acquire position knowledge of the target within the patient. Also, once the patient is positioned correctly with the transducer in place, a low-dose spot scan can be delivered at various depths within the patient to acquire range information of the treatment plan. Multiple depth deliveries would benefit the treatment planning aspect with more accurate knowledge of stopping power within the body. Since slightly more dose would be given for such a technique, a less thorough approach can be utilized where one depth is delivered for just beam range assurances. This "scout" scan can be used for adaptive pre-planning purposes. For purposes during the treatment, protoacoustics could provide a method of real-time range and dosimetric verification using the techniques shown previously. This would allow for online adaptive treatment where adjustments could be made while the treatment plan is being delivered. For post-treatment applications, the results obtained by the transducer could be used to compare to the log-file generated by the proton system for adaptive post-planning purposes. The log-file is generated after each beam is delivered, containing the range and charge output for each spot deposition for patient quality assurance applications.

To further progress on the clinical applications of this technique would be to measure protoacoustic signals resulting from dose depositions in a physical phantom representing a human body instead of a water tank. Such implementation would pose issues resulting from impedance mismatches at the surface interface in addition to within the phantom structure for differing materials representing bone and tissue. Another pathway would be for implementation of a two-dimensional transducer array for image reconstruction. This would present benefits for real-time imaging and internal organ motion management, in addition to an unconventional method of proton radiography.

Additional Example Methods

Proton induced acoustic range measurements were performed with a proton synchrocyclotron (Mevion S250i Hyperscan) at energies ranging from 45.5 MeV to 227.15 MeV, which correlates to $D_{90}$ depth distances of 1.9 cm to 32.2 cm. The $D_{90}$ depth is defined as the depth at which 90% of the distal portion of the Bragg peak occurs. The gantry of the system was positioned to deliver a horizontal beam into a water tank with an entrance window on the side to reduce attenuation of the beam. The extension was completely retracted and the isocenter of the system was set to be 15 cm from the entrance window of the tank, leaving an air gap of 18.6 cm. Since the central frequency of the induced signal was measured to be around 30 kHz in water with a proton dose deposition, a low-frequency 0.5 MHz transducer (Olympus V389-SU) was used. This transducer was positioned in the tank along the beam axis, with the surface of the transducer at a distance of approximately 34 cm from the entrance window of the tank. The transducer was placed approximately 10 cm from the water surface, which is low enough to reduce reflections. The transducer was then connected to a two-stage amplification system placed in a borated-polyethylene shielding box. The first stage preamplifier (Olympus 5660B Preamp) had 40 dB amplification and the second stage preamplifier (SRS SR560 Low-Noise Preamplifier) had a low noise amplification of 60 dB, with a set 6 dB bandwidth of 3 kHz to 100 kHz. This bandwidth was selected based on the frequency of the signal collected in order to effectively eliminate noise that occurs outside this bandwidth. This resulted in a maximum signal amplification of 100 dB. The signal was then connected to a dispatch board and sent outside the treatment room to the console patch panel to be connected and viewed on a digital oscilloscope (Rigol DS1202). Data on the oscilloscope was stored with a sampling time of 500 ns. A charge deposition of 1 pC corresponds to 0.0685 MU, therefore the smallest deposition of charge seen in patient treatments is approximately 4 pC. With this in mind, various datasets were gathered with charges-per-pulse ranging from 3 pC/pulse to 7 pC/pulse in order to ensure that the charge-per-pulse utilized was on the order of the smallest depositions seen in patient treatments.

A similar setup as in the range verification experiment was used. Single pulse signals were acquired with a charge-per-pulse deposition that varied from 2 pC/pulse to 9 pC/pulse. A beam energy of 162.78 MeV, which correlates to approximately 18 cm, was delivered with the transducer placed at a depth distance of 28 cm. The range variations along with the peak-to-peak voltage of the various signals were measured and analyzed.

To have an objective and consistent correlation point in the analysis of the range verification signals, dose induced acoustic signals were simulated in the k-wave toolbox. This point of analysis is essential in correlating the percent-maximum in the protoacoustic signal to the $D_{90}$ depth distance of the proton beam. Three-dimensional depth-dose data was obtained from commissioning of the proton system and was used to simulate the dose deposition for various beam energies. The dose files used had energies ranging from 200 MeV to 40 MeV. The resolution of the medium was chosen based on the resolution of the dose files, which varied from 0.5 mm to 0.1 mm. The sampling time and total collection time for the various simulation parameters were 0.1 μs and 25 μs, respectively. For a transducer in the medium that is placed 2 cm from the $D_{90}$ deposition and centered on the beam axis, the total collection time used is sufficient for total signal collection. The speed of sound used for the medium was 1498 m/s to represent that of distilled water.

It was preferred to run simulations with various beam energies since the spot size increases with increasing energy, which affects the signal compression on the time axis. Therefore, this would affect the correlation point since a percent-maximum method was utilized. The protoacoustic signals produced from the k-wave simulation were convolved with a square wave signal to simulate a pulse width of 4.0 μs.

In the simulation, the correlation point was calculated for each energy based on the speed of sound in the homogenous medium and the distance between the $D_{90}$ range of the beam and the placed position of the transducer in the simulation space. The percent-maximum of the induced signal at which the correlation point occurs was calculated for each beam energy simulated and then applied to the experimental data. The percent-maximum of the induced signal at which the correlation point occurs for each energy and pulse-width type is shown in Table 1.

TABLE 2. The percent-maximum of the induced signal at which the correlation point occurs for each beam energy simulated.

| Beam Energy [MeV] | Percent-Maximum |
|---|---|
| 200 | 0.8407 |
| 175 | 0.6450 |
| 150 | 0.5994 |
| 125 | 0.6112 |
| 100 | 0.6862 |
| 75 | 0.5644 |
| 40 | 0.3713 |

With the signals acquired in data collection, the time between the beam current trigger of the proton system and the percent maximum of the rising edge of the first peak of the protoacoustic signal was used to calculate the distance between the transducer and the $D_{90}$ range of the beam. This distance then infers the range of the proton dose deposition. A delay between the beam current trigger and a scintillator was measured to be 15.3 μs and was incorporated into the calculations. A typical ionaocustic signal can be seen in FIG.

10C, where the signal induced by the proton beam occurs approximately at 50 μs and the reflection signal from the wall of the tank occurs at approximately 350 μs. This signal was obtained with a 3 pC deposition and 1024 signal averaging on the oscilloscope.

Single pulse acquisitions are necessary with the implementation of pencil beam scanning in proton therapy, where single spots may be deposited once per location in the treatment plan. The feasibility of single pulse acquisition was explored by quantifying the SNR of the protoacoustic signal. Various amounts of signal averaging were utilized in data collection, and it was observed that a decrease in averaging produced a decrease in SNR of the protoacoustic signal. The SNR was calculated to depreciate from approximately 30 dB at 32 signal averages to approximately 5 dB with single pulse acquisitions with the implementation of a Savitzky-Golay filter. Without this filter, the SNR of the signal was approximately −5 dB, concluding that digital filtering is crucial in acquisitions of single pulse signals of adequate SNR. Based on the three ranges of averaging that result in different levels of SNR, three amounts of averaging were chosen to investigate the amount of SNR needed for a specific level of accuracy: 1024 averages, 4 averages, and single-pulse acquisitions.

CONCLUSION

In conclusion, the present embodiments provide a function workflow for 3D protoacoustic imaging with the input of real clinical treatment record. For the first time, these have been done using MC simulations that utilize real delivered treatment machine records rather than only using treatment plan parameters. The simulation workflow is robust to sample geometries and sensor geometries and can serve as a useful tool for investigations of the feasibility of proton therapy on a wide variety of proton machines for which the temporal radiation pulse profile is well known.

It has been shown that dose reconstruction is possible in protoacoustics using an array even if the SNR of all individual elements is <1, which implies that protoacoustic imaging may be more sensitive than previously thought as time reversal reconstruction can introduce an 'averaging' effect as noisy signals are time-reversed into the simulation geometry.

It has also been shown that it is possible to generate high frequency signals from longer pulses if the rise time of the pulses is sufficiently sharp (so long as the spatial distribution of the beam has sufficiently sharp gradients). This provides an explanation of previous experiments where such phenomena was observed experimentally with x-ray beams. The present disclosure demonstrates the importance of future proton machines to try and maximize spatial heat gradients and minimize pulse width for the sake of protoacoustic imaging, as a strong signal from a proton source can be used to enable image guidance. Additionally, provided here is an explanation for why in certain conditions, beams with large pulse durations on the order of several μs can generate MHz acoustic signals.

It is believed that protoacoustic imaging can enable 3D, high-resolution, real-time mapping of proton dose during radiation therapy. Through the workflow demonstrated here, researchers can conveniently model protoacoustic imaging and enable further development of this technology towards clinical application.

The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably coupleable," to each other to achieve the desired functionality. Specific examples of operably coupleable include but are not limited to physically mateable and/or physically interacting components and/or wirelessly interactable and/or wirelessly interacting components and/or logically interacting and/or logically interactable components.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

Although the present embodiments have been particularly described with reference to preferred examples thereof, it should be readily apparent to those of ordinary skill in the art that changes and modifications in the form and details may be made without departing from the spirit and scope of the present disclosure. It is intended that the appended claims encompass such changes and modifications.

What is claimed is:

1. A system for generating protoacoustic images in real time, including:
- an ultrasound transducer adapted to receive proton induced acoustic signals generated from a proton source during proton therapy; and
- a protoacoustic imaging unit adapted to receive signals from the ultrasound transducer and generate a reconstructed image for assisting the proton therapy, wherein the protoacoustic imaging unit is adapted to generate the reconstructed image by performing k-wave simulations of signals received by the ultrasound transducer to generate relative protoacoustic pressure maps.

2. The system of claim 1, wherein the protoacoustic imaging unit is further adapted to generate the reconstructed image by localizing a Bragg peak and measuring a radiation dose of the proton source in vivo.

3. The system of claim 1, further comprising a trigger sequencing logic device that triggers proton induced acoustic signal acquisition in correspondence with a dose provided by the proton source.

4. The system of claim 1, wherein the protoacoustic imaging unit is adapted to generate the reconstructed image by co-registering the signals from the ultrasound transducer with a scouting CT scan.

5. The system of claim 1, wherein the ultrasound transducer comprises an array of transducers.

6. The system of claim 1, wherein a pulse shape of the proton source is optimized for generating the reconstructed image.

7. The system of claim 1, wherein a pulse width duration of the proton source is optimized for generating the reconstructed image.

8. The system of claim 1, wherein a single dose from the proton source is used for generating the reconstructed image.

9. The system of claim 1, wherein a plurality of doses from the proton source is used for generating the reconstructed image.

10. A method for generating protoacoustic images in real time, including:
- receiving, from an ultrasound transducer, proton induced acoustic signals generated from a proton source during proton therapy; and
- generating, by a protoacoustic imaging unit adapted to receive signals from the ultrasound transducer, a reconstructed image for assisting the proton therapy, wherein generating the reconstructed image includes performing k-wave simulations of signals received by the ultrasound transducer to generate relative protoacoustic pressure maps.

11. The method of claim 10, wherein generating the reconstructed image further includes localizing a Bragg peak and measuring a radiation dose of the proton source in vivo.

12. The method of claim 10, further comprising triggering, by a trigger sequencing logic device, proton induced acoustic signal acquisition in correspondence with a dose provided by the proton source.

13. The method of claim 10, wherein generating the reconstructed image includes co-registering the signals from the ultrasound transducer with a scouting CT scan.

14. The method of claim 10, further comprising optimizing a pulse shape of the proton source for generating the reconstructed image.

15. The method of claim 10, further comprising optimizing a pulse width duration of the proton source for generating the reconstructed image.

16. The method of claim 10, wherein a single dose from the proton source is used for generating the reconstructed image.

17. The method of claim 10, wherein a plurality of doses from the proton source is used for generating the reconstructed image.

18. The system of claim 4, wherein the scouting CT scan is performed using x-ray computed tomography.

19. The method of claim 13, wherein the scouting CT scan is performed using x-ray computed tomography.

* * * * *